United States Patent
Rubio Martinez et al.

(10) Patent No.: US 10,525,440 B2
(45) Date of Patent: *Jan. 7, 2020

(54) PRODUCTION OF METAL-ORGANIC FRAMEWORKS

(71) Applicant: Commonwealth Scientific and Industrial Research Organisation, Acton, Australian Capital Territory (AU)

(72) Inventors: Marta Rubio Martinez, Clayton South (AU); Matthew Roland Hill, Clayton South (AU); Michael Batten, Clayton South (AU); Kok Seng Lim, Clayton South (AU); Anastasios Polyzos, Clayton South (AU); Timothy Raymond Barton, Clayton South (AU); Trevor Dean Hadley, Clayton South (AU); Andreas Alexander Monch, Clayton South (AU)

(73) Assignee: Commonwealth Scientific and Industrial Research Organisation (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,413

(22) Filed: Mar. 8, 2019

(65) Prior Publication Data
US 2019/0201866 A1  Jul. 4, 2019

Related U.S. Application Data

(63) Continuation of application No. 15/172,942, filed on Jun. 3, 2016, now Pat. No. 10,272,412, which is a
(Continued)

(51) Int. Cl.
*B01J 19/24* (2006.01)
*B01J 31/02* (2006.01)
(Continued)

(52) U.S. Cl.
CPC ....... *B01J 19/2435* (2013.01); *B01J 19/0006* (2013.01); *B01J 19/242* (2013.01);
(Continued)

(58) Field of Classification Search
CPC .. B01J 19/2435; B01J 19/243; B01J 19/2405; B01J 19/24; B01J 19/242; B01J 19/2425;
(Continued)

(56) References Cited

U.S. PATENT DOCUMENTS

| 1,213,143 A | 1/1917 | Aylsworth |
| 2014/0069456 A1 | 3/2014 | Lee et al. |

(Continued)

FOREIGN PATENT DOCUMENTS

| EP | 2 404 666 A1 | 1/2012 |
| WO | 2012/167315 A1 | 12/2012 |

(Continued)

OTHER PUBLICATIONS

International Search Report and Written Opinion of the International Searching Authority for International Patent Application No. PCT/AU2015/000317 (dated Jul. 20, 2015).
(Continued)

*Primary Examiner* — Lessanework Seifu
(74) *Attorney, Agent, or Firm* — Merchant & Gould P.C.

(57) ABSTRACT

An apparatus for producing metal organic frameworks, comprising: a tubular flow reactor comprising a tubular body into which, in use, precursor compounds which form the metal organic framework are fed and flow, said tubular body including at least one annular loop.

18 Claims, 9 Drawing Sheets

Related U.S. Application Data continuation of application No. 14/545,594, filed on May 27, 2015, now Pat. No. 9,630,163, and a continuation of application No. PCT/AU2015/000317, filed on May 27, 2015.

(51) Int. Cl.

| | | |
|---|---|---|
| *B01J 20/22* | (2006.01) | |
| *B01J 31/16* | (2006.01) | |
| *B01J 31/22* | (2006.01) | |
| *B01J 19/00* | (2006.01) | |
| *B01J 31/12* | (2006.01) | |
| *C07F 1/08* | (2006.01) | |
| *C07F 5/00* | (2006.01) | |
| *C07F 5/06* | (2006.01) | |
| *C07F 7/00* | (2006.01) | |

(52) U.S. Cl.
CPC ............ *B01J 19/243* (2013.01); *B01J 20/226* (2013.01); *B01J 31/12* (2013.01); *B01J 31/1691* (2013.01); *B01J 31/2239* (2013.01); *C07F 1/08* (2013.01); *C07F 5/00* (2013.01); *C07F 5/06* (2013.01); *C07F 7/00* (2013.01); *B01J 2219/00087* (2013.01); *B01J 2219/00162* (2013.01); *B01J 2219/24* (2013.01); *B01J 2531/0216* (2013.01); *B01J 2531/0219* (2013.01); *B01J 2531/16* (2013.01); *B01J 2531/35* (2013.01); *B01J 2531/48* (2013.01)

(58) Field of Classification Search
CPC ............ B01J 20/226; B01J 2219/00004; B01J 2219/00015; B01J 2219/00094; B01J 2219/00099; B01J 2219/00033; B01J 2219/00192
See application file for complete search history.

(56) References Cited

U.S. PATENT DOCUMENTS

| | | |
|---|---|---|
| 2014/0326007 A1 | 11/2014 | Dinca et al. |
| 2015/0182936 A1 | 7/2015 | Kim et al. |

FOREIGN PATENT DOCUMENTS

| | | |
|---|---|---|
| WO | 2013/086585 A1 | 6/2013 |
| WO | 2014/013274 A2 | 1/2014 |

OTHER PUBLICATIONS

Australian Examination Report for Australian Patent Application No. 2015203627 (dated Jul. 24, 2015).
Australian Examination Report for Australian Patent Application No. 2015203627 (dated Sep. 30, 2015).
Bayliss et al., "Synthesis of metal-organic frameworks by continuous flow", Green Chemistry, 16:3796-3802 (2014).
Faustini et al., "Microfluidic Approach toward Continious and Ultrafast Synthesis of Metal-Organic Framework Crystals and Hetero Structures in Confined Microdroplets", Journal of the American Chemical Society, 135:14619-14626 (2013).
Gimeno-Fabra et al., "Instant MOFs: continuous synthesis of metal-organic frameworks by rapid solvent mixing", Chem. Commun., 48:10642-10644 (2012).
Kim et al., "High-rate synthesis of Cu-BTC metal-organic frameworks", Chem. Commun., 49: 11518-11520 (2013).
Paseta et al., "Accelerating the Controlled Synthesis of Metal-Organic Frameworks by a Microfluidic Approach: A Vanoliter Continuous Reactor", ACS Applied Materials & Interfaces, 5:9405-9410 (2013).
Rubio-Martinez et al., "Versatile, High Quality and Scalable Continuous Flow Production of Metal-Organic =Frameworks", Scientific Reports, 4, 5443:1-5 (Jun. 25, 2014).
Waitschat et al., "Flow-synthesis of carboxylate and phosphonate based metal-organic frameworks under non-solvothermal reaction conditions", Dalton Trans., 44: 11235-11240 (2015).

|   | Cu²⁺ [M] | T (°C) | Residence Time (min) | Yield (%) | SA$_{BET}$ (m² g⁻¹) |
|---|---|---|---|---|---|
| 1 | 0.005 | 80  | 1  | 80   | 890  |
| 2 | 0.005 | 80  | 2  | 31.3 | 1030 |
| 3 | 0.005 | 140 | 2  | 71.4 | 993  |
| 4 | 0.02  | 140 | 1  | 97.8 | 1298 |
| 5 | 0.05  | 140 | 1  | 100  | 1932 |
| 6 | 0.1   | 80  | 1  | 58   | 1600 |
| 7 | 0.1   | 80  | 10 | 61   | 1755 |
| 8 | 0.1   | 80  | 2  | 74   | 1852 |
| 9 | 0.1   | 140 | 1  | 78   | 2046 |

(A)

Al-Fumarate supernatant (B)

MIL-53 (Al) supernatant

PRODUCTION OF METAL-ORGANIC FRAMEWORKS

This application is a Continuation of U.S. patent application Ser. No. 15/172,942, filed 3 Jun. 2016, which is a Continuation of U.S. patent application Ser. No. 14/545,594, filed 27 May 2015, now U.S. Pat. No. 9,630,163, and a Continuation of International Patent Application No. PCT/AU2015/000317, filed 27 May 2015 and which applications are incorporated herein by reference. To the extent appropriate, a claim of priority is made to each of the above disclosed applications.

TECHNICAL FIELD

The present invention generally relates to an apparatus, process and system for the production of metal-organic frameworks. The invention is particularly applicable for production of metal-organic frameworks (MOFs) and it will be convenient to hereinafter disclose the invention in relation to those exemplary applications.

BACKGROUND OF THE INVENTION

The following discussion of the background to the invention is intended to facilitate an understanding of the invention. However, it should be appreciated that the discussion is not an acknowledgement or admission that any of the material referred to was published, known or part of the common general knowledge as at the priority date of the application.

Metal-Organic Frameworks (MOFs) are a class of promising porous materials having tunable functionality, large pore sizes and the highest known surface areas. These characteristics are of high interest for a myriad of industrial applications such as gas storage, gas separation, drug delivery and catalysis. However, to date the cost of these materials has remained prohibitively high, thereby restricting the ability of these materials to make a significant impact on prospective markets or technologies. Very few MOFs described in academic literature are commercially available, with that availability limited to small quantities (grams).

An important requirement for accessing the potential applications of MOFs is the ability to routinely synthesise MOF materials in large quantities (kg scale or higher) at an economic price point. Such a process needs to be a versatile, efficient and scalable synthesis that is able to produce MOFs in large quantities in order to introduce these materials to real world applications.

However, traditional laboratory routes such as the classical solvothermal synthesis are difficult to scale up due to the extended reaction times (~24 hours) and low quality material yield. Furthermore, a wide variety of available synthetic synthesis methods have a singular nature providing an inherent inflexibility for any prospective production process.

One of the barriers to scaled-up MOF synthesis is that commonly MOFs nucleate at a reaction surface, meaning that the size of the reaction vessel becomes a significant parameter in the synthesis conditions. Consequently, reactions that proceed in small lab scale conditions are not always successful when scaled up into larger vessels, limiting scaled up MOF chemistry to a small number of MOFs that are robust in their preparation, each requiring bespoke equipment. Therefore a method to conveniently expand the scale of production, keep sufficient residence times, while minimising vessel geometry is extremely attractive to applied MOF chemistry, offering a versatile route to production.

Continuous flow chemistry is renowned as a paradigm shifting approach to chemical synthesis. The improved heat and mass transfer available often leads to improved reaction yields, reduced reaction times, faster reaction syntheses, new synthetic pathways, and broader green chemistry implications.

Recent studies have reported that it is possible for MOFs to be produced by continuous processes. Gimeno-Fabra M. et al. Instant MOFs: continuous synthesis of metal-organic frameworks by rapid solvent mixing. Chem. Commun. 48, 10642-10644 (2012) showed that use of a bespoke tube-in-tube, counter-current mixing reactor at the high temperature of 300° C. can lead to MOFs. It was also shown that small amounts of MOFs, within oil droplets, can be made in microfluidic reactors (see Faustini M. et al. Microfluidic Approach toward Continuous and Ultra-Fast Syn-thesis of Metal-Organic Framework Crystals and Hetero-Structures in Confined Microdroplets. J. Am. Chem. Soc. 135, 14619-14626 (2013) and Paseta L. et al. Accelerating the controlled synthesis of MOFs by a microfluidic approach: a nanoliter continuous reactor. ACS Appl. Mater. Interfaces 5, 9405-9410 (2013)). In 2013 Kim K.-J. et al. (High-rate synthesis of Cu-BTC metal-organic frameworks. Chem. Commun. 49, 11518-11520 (2013)) reported a proof of concept mesoscale flow production of HKUST-1 using a continuos flow reactor comprising a 30 cm long and 1.59 mm I.D. stainless steel pipe. It is noted that the MOFs produced had moderate surface area at low scale. All of these early reports are promising steps towards production of MOFs at scale. However, in order for this to be viable, pure MOFs must be readily attainable without a loss in product quality.

Given the wide array of MOFs known, and the likelihood of a large range of applications each requiring different MOFs in the future, a versatile production technique is crucial. It would therefore be desirable to provide a new and/or improved method and apparatus for producing MOFs.

SUMMARY OF THE INVENTION

The present invention provides a new and/or improved apparatus, system and process for producing a metal organic framework.

A first aspect of the present invention provides an apparatus for producing metal organic frameworks, comprising: a tubular flow reactor comprising a tubular body into which, in use, precursor compounds which form the metal organic framework are fed and flow, said tubular body including at least one annular loop.

A second aspect of the present invention provides use of a tubular flow reactor for producing metal organic frameworks, wherein the tubular flow reactor comprises a tubular body including at least one annular loop, and in use precursor compounds for forming the metal organic framework are fed and flow through the tubular body.

The present invention provides a continuous flow chemistry process, system and apparatus for the production of MOFs which is applicable to a large number of MOFs with different reaction conditions. Continuous flow production of MOF materials allows MOFs to be continuously produced for extended periods of time. Furthermore, a continuous flow approach can provide a reaction rate that is higher, typically significantly higher than any previously reported values, and is capable of producing at higher space time yields than other commercial manufacturing processes. The process of the present invention is further scalable without a losses in yield or surface area of the material with concomitant control over particle size. The apparatus and process of the present invention therefore demonstrate production quantities approaching those required for broad application.

It should be understood that flow reactors may also be referred to herein as continuous flow reactors. Furthermore, it should be appreciated that the features discussed below in connection with the first aspect of the present invention (a tubular flow reactor) equally apply to the second aspect of the present invention (use of a tubular flow reactor).

The advantage of the present process and apparatus over prior processes is in at least part a result of the configuration of the tubular flow reactor. The tubular flow reactor of the present invention comprises at least one annular loop, and preferably a plurality of annular loops. In exemplary embodiments, the tubular flow reactor comprises a coil or coiled reactor. A coil reactor advantageously allows precise and homogeneous control of the temperature and mixing of the reagents, reducing the reaction time, achieving highest material quality, highest yields and control over the particle size. The coil tubular body of the tubular flow reactor of the present invention therefore enables more homogeneous heating and better mixing and as consequence higher quality materials and less reaction time in comparison to prior published studies of MOFs produced by continuous processes. Other reactors may be employed to suit the design of ancillary equipment or varied process conditions. For example where prolonged contact with the energy transfer device is less critical a tube-in-shell reactor arrangement may be employed to give higher throughput. However an annular loop configuration is preferred as it allows efficient energy transfer to the reaction mixture using a very simple design that has a low cost to manufacture.

The at least one conduit of the tubular reactor of the present invention includes a device, element or arrangement which supplies energy to the reaction mixture. This energy can be, but is not limited to heat, electromagnetic energy, sonic energy. The tubular reactor itself is preferably designed such that the transfer of energy to the reaction mixture is as efficient as possible and may therefore be in the form of a single tube, tube and shell, plate and frame, pillow panel or complex-structured reactor type.

The annular loops of the tubular body can be arranged in any suitable configuration. The annular loops of the tubular body may be curved through 0 to 360 degrees of curvature in any direction and any curves may be reversed or orthogonal to previous or following curved sections of the tubular body. The annular loops may follow an open loop (including straight), serpentine or annular/helical configurations. The diameter of the tubular body may vary along its length and structures or surface treatments included inside the tubular body to alter the flow path of the materials passing through it. The tubular body may be permeable along its length to allow the introduction or withdrawal of fluids to or from the tubular body. In some embodiments, each annular loop is radially centred about and axially spaced along a central axis. The annular loops can therefore form a substantially tubular shaped coil radially centred about the central axis. Again, in exemplary embodiments the annular loops comprise a coil, preferably a helical coil. In some embodiments, the tubular flow reactor comprises a capillary tubular flow reactor. However, it should be appreciated that not all embodiments are necessarily capillary tubular flow reactors. It should be understood that the internal diameter of the tubular body of the tubular flow reactor can be sized for various applications. In some embodiments, the internal diameter of the tubular body is between 0.5 mm and 50 mm, preferably between 1 and 25 mm, more preferably from 1 to 15 mm.

The dimensions and configuration of each annular loop can vary depending on the application and scale of production. In embodiments, the average radius of each annular loop is between 10 and 1000 mm. In other embodiments, the average radius of each annular loop is between 20 and 500 mm, preferably between 40 and 200 mm. Similarly, in some embodiments the length of the coil is greater than 50 mm, preferably greater than 100 mm, more preferably between 20 and 200 mm. In some embodiments, the length of the coil is between 200 and 1000 mm. It should be noted that the uncoiled length of the tube would be significantly longer, in some cases being in excess of 10 m, in some cases in excess of 20 m.

The tubular body of the tubular flow reactor can comprise one or more length of coil. In some embodiments, the tubular body comprises a single length of coil. In other embodiments, the tubular body comprises at least two fluidly connected coils. It should be understood that those fluidly connected coils could be connected in series and/or parallel within the overall tubular flow reactor. In some embodiments, the fluidly connected coils are connected in series to increase the reactor length of the tubular body. In some embodiments, the fluidly connected coils are connected in parallel in order to increase the flow capacity of the tubular body. A combination of parallel and series connected coils can also be used. It is noted that a parallel, multiple coil arrangement would enable a multiple component MOF to be thermally treated in stages and then do a final pass through the same heated vessel.

It should be appreciated that flow reactors can readily be operated with multiple flow lines making the scale up to large production quantities relatively straight forward. In particular, it can be more effective and efficient to "number-up" (i.e. scale up through repetition or replication) flow lines to produce a given quantity of MOF. For example, a flow reactor for producing 0.2 g/unit time of MOF material can be readily be "numbered up" to produce, 2 g, 20 g, 200 g or 2 kg/unit time etc. of MOF material. In one embodiment, the flow reactor is a tubular coil flow reactor in which the tubular body is constructed of perfluoroalkoxy alkane (PFA) or metal, for example stainless steel. However, it should be appreciated that the tubular body could be constructed of any suitable material including various plastics, metals, ceramics or the like. In this respect, the materials of construction (and wall thicknesses) are preferably selected to deal with the temperature and pressure required in the reactor, and are chemically compatible with the reagents, MOF product and byproducts. It should be appreciated that the internal surface of the tubular body can be coated to activate reactions, or repress side reactions, or for other purposes.

It should be appreciated that the use of annular loops, preferably coils in the tubular reactor can allow very high surface are for a small footprint. High surface area increases the amount of MOF that can be produced by the apparatus, in some cases allowing many kgs of MOF to be produced using the apparatus of the present invention. In some cases, coiling may also assist in the prevention of clogging/blockage of the tubes of the tubular reactor via the velocity/annular velocity and centrifugal force of the fluid generated therein.

It should be appreciated that the use of annular loops, preferably coils in the tubular reactor can allow very high surface are for a small footprint. High surface area increases the amount of MOF that can be produced by the apparatus, in some cases allowing many kgs of MOF to be produced using the apparatus of the present invention. In some cases, coiling may also assist in the prevention of clogging/blockage of the tubes of the tubular reactor via the velocity/annular velocity and centrifugal force of the fluid generated therein.

The tubular body is preferably heated. The tubular body can be heated by any suitable arrangement. In some embodiments, the tubular body is covered by or otherwise in contact with a heating arrangement, for example a heating element or the like. In some embodiments, a heating fluid such as gas or liquid is ultilised. In other embodiments, the tubular body can be heated by a number of means including gas (such as air, post combustion gases, steam), liquid (water, heating fluid such as silicone oil), or electrically. In some embodiments, the tubular body is located inside a heated housing. The precursor compounds flowing through the tubular body are heated to a suitable temperature conducive to MOF formation from these precursor compounds. The particular temperature depends on the reaction chemistry and desired reaction kinetics in forming a particular MOF. However, in a number of embodiments the tubular body heats the precursor compounds to a temperature of between 20 and 200° C., preferably between 25 and 150° C., more preferably between 25 and 130° C.

In some embodiments, the energy source for the synthesis of MOFs in the tubular flow reactor is photochemical in nature. In other embodiments the energy source is light based. In other embodiments, the energy source may result from ultrasonication, microwave heating, cooling, or the like.

The preferred pressure in the reactor is between 0 and 30 bar, preferably between 5 and 10 bars. However, it should be appreciated that pressure is a function of temperature of the fluid and therefore may vary accordingly.

It should be appreciated that the tubular flow reactor of the present invention can include any number of additional features including (but not limited to) in-line monitoring of reaction conditions, optical, thermal, pH probes, conductivity probes/sensors, particle size distribution (PSD), UV, IR, Laser Induced Breakdown Spectroscopy (LIBS) and the like.

A third aspect of the present invention provides a process for producing metal organic frameworks which comprises:

introducing into an apparatus according to the first aspect of the present invention a solution comprising precursor compounds for forming the metal organic framework in solvent; and promoting a reaction within the tubular flow reactor to form the metal organic framework.

It should be appreciated that in embodiments, the apparatus can continuously run to produce at least 1 kg/hr, preferably 2 kg/hr. However, it should be appreciated that the production rate will vary for each different MOF because each MOF has different molecular weight and different reactant and product concentrations. Furthermore, the yield of MOF from the apparatus is preferably greater than 60%, more preferably greater than 80%, and in some embodiments greater than 95%. For example, for in embodiments, the maximum yield is 100% (for the Aluminium Fumarate) using in both cases the maximum concentration of precursors based on their solubility.

The precursor compounds can be introduced into the apparatus in a variety of different regimes. In some embodiments, the precursor compounds are provided in at least two different precursor solutions containing different precursor compounds, the precursor solution being mixed prior to introduction into the tubular body. In these embodiments, the precursor solutions are preferably mixed within a mixing vessel prior to introduction into the tubular body. It should be appreciated that precursors can either be dissolved in the solution or be provided as an undissolved component/solid for example a dispersion.

In other embodiments, the precursor solutions are mixed through inline mixing in a feed conduit fluidly connected to an inlet of the tubular body. A number of inline mixing arrangements can be used. For example, inline mixing can comprises one or more mixing joints, preferably T-Y- or cross junctions, annular feed systems or a plethora of channels between feed flows of the two or more precursor solutions, such that mixing of the components occurs in an optimal manner. In some embodiments, the mixing arrangement comprises an mixing element which is insertable into one or more of the conduits. In some embodiments, the precursor solutions are mixed using static mixers. Static mixer may be easier to use for reaction tubes of larger internal diameter. A static mixer or mixer present in a conduit may not be heated directly, but rather receive heat, via conduction (i.e. in direct contact with the conduit) or via convection. The static mixers can be incorporated into the tube before entry into the reactor, or in the tube which is in the heated zone, or both. As such, the static mixer section can be heated in any of these placements. Heating to the static mixer would be via conduction (if the static mixer is in direct/intimate contact with the internal wall of the tube, or via convection. Different shapes/geometries of static mixers are possible and would be a function of the degree of mixing/flow patterns required, and possibly to facilitate/tune the balance between nucleation vs particle growth.

In yet other embodiments, the precursor compounds are provided in at least two different precursor solutions containing different precursor compounds, the precursor solutions being mixed after introduction into the tubular body. It should be appreciated that the different precursor solutions can be fed into the same inlet or separate inlets. However, where the different precursor solutions are fed into the same inlet, it is preferable that the two or more precursor solutions are mixed at or proximate that inlet.

The apparatus of the present invention preferably includes a flow restriction device downstream of the tubular reactor to control/set the desired pressure required in the reactor. Preferably, the flow restriction device maintains a constant the pressure of the flow stream in the reactor. The flow restriction device may be in the form of a back-pressure controller of fixed spring loading, manually set or of automated design. Alternatively the flow restriction device may be a simple valve operated manually or via an automated control system, or a fixed orifice. In some embodiments, the flow restriction device comprises a diaphragm sensing back pressure regulator from Swagelok (Series KBP). Control of the flow restrictor may be linked to operation of the tubular reactor by feedback loop for example using pressure or temperature sensors and the degree of flow restriction varied to control the pressure or pressure profile achieved in the reactor during operation. The back pressure regulator is located after the reactor and used to prevent the reaction product, the MOFs, from blockage up the reaction tube and preventing continuous flow It has been surprising to find that particulate compounds, such as MOFs, can be made in such small diameter tubing without blockage and that the use of annular loops and back pressure regulation has allowed continuos production of kilograms of material over very short periods of time.

In some embodiments of the present invention, the process further comprises the step of:

separating the MOF from the MOF containing solution.

This separation can be achieved using a number of unit processes, including centrifuging, filtration or the like. However, in some embodiments, this separation is achieved using the step of:

applying a high frequency ultrasound of at least 20 kHz, preferably between 20 to 4 MHz, more preferably 500 kHz to 2 MHz, yet more preferably between 800 kHz and 2 MHz, and yet more preferably between 1 MHz and 2 MHz to the MOF containing solution to a MOF containing solution sourced from the tubular flow reactor, thereby substantially separating the MOF material from solution as an aggregated sediment which settles out of the MOF containing solution.

In some embodiments, the apparatus of the first and second aspects of the invention can similarly further include an ultrasonic and/or megasonic separation apparatus. Thus, in some embodiments the system and apparatus further includes an apparatus for separating a metal organic framework (MOF) from a solution, comprising:

a housing having a reservoir capable of receiving a MOF containing solution; and a high frequency ultrasound transducer operatively connected to the reservoir and capable of applying frequencies of at least 20 kHz, preferably between 20 to 4 MHz, more preferably 500 kHz to 2 MHz, yet more preferably between 800 kHz and 2 MHz, and yet more preferably between 1 MHz and 2 MHz to the MOF containing solution to the MOF containing solution.

The separation apparatus uses a high frequency ultrasound and is applied to that MOF containing solution to effect separation of the MOF from the solution. The apparatus can also be used for a washing or purification method, in which the MOF includes at least one contaminant and the apparatus is used to separate those contaminants from the MOF in solution.

It should be appreciated that the separation apparatus could be integrally incorporated into the structure of the tubular reactor to form a single apparatus or arrangement. Alternatively, the separation apparatus could be connected, preferably fluidly connected to the tubular reactor, and thus provided a further unit/process step in the overall MOF production process.

It should be appreciated that separation in this washing and purifying context broadly encompasses a number of unit processes including washing processes, purification processes, polishing processes and the like. All of these processes involve the separation of a product (in the present invention a MOF) from a contaminant or other material. It should be appreciated that all these process functions and similar processes are incorporated into the scope of the present invention.

Ultrasonic separation involves the application of high frequency ultrasound or megasonic frequencies of >20 kHz to a MOF containing solution. Acoustic radiation from the applied frequencies aggregate MOFs towards pressure nodes formed within the MOF-containing solution. The aggregated MOF material tends to sediment out of solution at a greatly accelerated rate to the bottom of a container or separation chamber housing the MOF containing solution. Ultrasonic and/or megasonic operation involves no moving parts, has a low surface area of contact with the fluid (i.e. lower capacity for fouling, ease of cleaning) and allows continuous separation, washing and/or purification of MOFs. Furthermore, the simplicity and speed of the process enables the process to be scaled, and applied economically to an existing MOF production method.

In many embodiments, the apparatus for separating a metal organic framework (MOF) further includes an acoustic reflector surface spaced apart from the transducer within the housing, the transducer, in use, being operated to reflect said applied high frequency ultrasound off the acoustic reflector surface. The transducer is therefore operated to apply a high frequency ultrasound to the MOF containing solution and to reflect said applied ultrasound from the acoustic reflector surface. The use of an acoustic reflector surface assists in the formation of a standing wave field required to form pressure nodes where particles are collected for cleaning or separation. This substantially separates the MOF material from solution as a aggregated sediment which settles out of the MOF containing solution.

The acoustic reflector surface is generally located in front of the transducer, and spaced apart from that transducer. In some embodiments, the transducer is located proximate or at one wall or side of the housing, and the acoustic reflector surface is located proximate or at an opposite wall or side of the housing.

The frequency of the applied high frequency ultrasound is important in the function and effect of the separation. Whilst the preferred frequency depends on factors such as MOF composition, particle size, solution composition and the like, the general ranges of applied high frequency ultrasound are as follows: In some embodiments, the applied high frequency ultrasound is between 20 to 4 MHz, preferably 500 kHz to 2 MHz, more preferably between 800 kHz and 2 MHz, and yet more preferably between 1 MHz and 2 MHz. In some embodiments, the applied high frequency ultrasound is greater than 1 MHz, preferably between 1 MHz and 10 MHz, and more preferably between 1 and 4 MHz.

In some cases, it can be advantageous to move the applied high frequency ultrasound between a high frequency and a low frequency. In some embodiments, the applied high frequency ultrasound is cycled between a high frequency and a low frequency. Again, the selected frequencies depend on a number of factors. However, in some embodiments the high frequency is between 400 kHz to 2 MHz and the low frequency is between 20 kHz to 400 kHz. However, other embodiments the low frequency is between 20 kHz to 500 kHz and the high frequency is between 500 kHz to 2 MHz.

The energy density of the applied high frequency ultrasound is another factor which can effect separation. In some embodiments, the energy density of the applied high frequency ultrasound is at least 25 kJ/kg, preferably between 100 kJ/kg to 250 kJ/kg.

In some embodiments, the process and apparatus of the present invention has the ability to achieve specificity of separation based on particle size by tuning of the operation parameters such as frequency and energy density. Thus, in some embodiments at least one of frequency or energy density of the applied high frequency ultrasound is tuned to selectively separate MOF and contaminants based on a specific particle size.

MOF material is extremely porous and therefore contaminant species in a solution can be trapped or otherwise located in the pores of the MOF material. The process of the present invention can be used for separation and/or purification of MOFs from such contaminants, and more particularly contaminants in the pores of a MOF. Thus, in some embodiments, the metal organic framework (MOF) includes at least one contaminant, and the method substantially separates the contaminant from the MOF within the solution. The contaminant is preferably left in solution and the MOF settles at or proximate to the bottom of the solution. Again, this separation includes contaminants in the pores of the MOF.

The Applicant considers that the size, material and/or geometry of the vessel or housing used for ultrasonic and/or megasonics separation/activation may have an effect on the outcome (degree, efficiency or the like) of ultrasonic and/or megasonic separation process of MOFs. Similarly, the positioning, arrangement and alignment of transducers within a separation apparatus may have an effect on the outcome (degree, efficiency or the like) of ultrasonic and/or megasonic separation process of MOF.

The transducer can be positioned in any suitable location in relation to the housing to apply the ultrasonic and/or megasonic frequencies to the MOF containing liquid received within the reservoir. In some embodiments, the housing comprises a container including at least one wall position to contact the MOF containing solution, and the transducer is high frequency ultrasound transducer which is positioned within the reservoir or in engagement with the at least one wall. In each case, the transducer is operable to apply ultrasonic and/or megasonic frequencies to a MOF containing solution housed in the reservoir.

The transducer can comprise any suitable high frequency ultrasound transducer. In some embodiments, the high frequency ultrasound transducer comprises a plate transducer.

The acoustic reflection of the applied frequencies can assist the MOF separation process. Accordingly, in some embodiments the housing includes at least one reflector surface designed to reflect the applied frequencies within the reservoir.

The MOF content is preferably separated from the solution following sedimentation at the bottom of the solution. The process therefore preferable further comprises the step of separating the MOF from the solution. Separation can be achieved using any number of separation process steps including but not limited to decanting, filtration, evaporation, centrifugation, gravity separation, flotation, magnetic separation, spray drying or the like.

A fourth aspect of the present invention provides a system for producing a metal organic framework (MOF), comprising:

an apparatus for forming a metal organic framework from precursor materials according to the first aspect of the present invention; and an apparatus for washing and/or purifying the metal organic framework, comprising: a housing having a reservoir capable of receiving a MOF containing solution from the reactor; and a high frequency ultrasound transducer operatively connected to the reservoir and capable of applying frequencies of at least 20 kHz, preferably between 20 to 4 MHz, more preferably 500 kHz to 2 MHz, yet more preferably between 800 kHz and 2 MHz, and yet more preferably between 1 MHz and 2 MHz to the MOF containing solution to the MOF containing solution.

In many embodiments, the apparatus for washing and/or purifying the metal organic framework further includes an acoustic reflector surface spaced apart from the transducer within the housing, the transducer, in use, being operated to reflect said applied high frequency ultrasound off the acoustic reflector surface.

A large variety of MOFs or MOF materials can be produced using the apparatus, process and system of the present invention.

It should be appreciated that Metal Organic Frameworks (MOFs) (also known as coordination polymers) or MOFs are a class of hybrid crystal materials where metal ions or small inorganic nano-clusters are linked into one-, two- or three-dimensional networks by multi-functional organic linkers. In this sense, MOF is a coordination network with organic ligands containing potential voids. A coordination network is a coordination compound extending, through repeating coordination entities, in one dimension, but with cross-links between two or more individual chains, loops, or spiro-links, or a coordination compound extending through repeating coordination entities in two or three dimensions and finally a coordination polymer is a coordination compound with repeating coordination entities extending in one, two, or three dimensions.

MOFs have many appealing features having surface areas of thousands of square meters per gram, extremely low density, interconnected cavities and very narrow porosity distributions. A variety of open micro- and mesoporous structures can be developed, leading to materials with extreme surface area.

Examples of metal organic frameworks which may be suitable for use in the present invention include those commonly known in the art as MOF-177, MOF-5, IRMOF-1, IRMOF-8, Al-fum (Aluminium fumarate) and MIL-53 (aluminium terephthalate) Zr-Fum (Zirconium fumarate), UiO-66, HKUST-1, NOTT-400, MOF-. It should be appreciated that the present invention is suitable for use with a large number of MOFs and should therefore not be limited to the exemplified MOF structures in the present application.

MOFs used in the process of the present invention preferably comprise a plurality of metal clusters, each metal cluster including one or more metal ions; and a plurality of charged multidentate linking ligands connecting adjacent metal clusters. Such MOFs can therefore be more generally defined by the charged multidentate linking ligands connecting adjacent metal clusters which are used to form each MOF. The MOF precursors can include one or more of the metal cluster or a metallic salt thereof and/or the multidentate linking ligands which form the final MOF.

Each metal cluster preferably includes one or more metal ions. As used herein, the term "cluster" means a moiety containing one or more atoms or ions of one or more metals or metalloids. This definition embraces single atoms or ions and groups of atoms or ions that optionally include ligands or covalently bonded groups. Each cluster preferably comprises two or more metal or metalloid ions (hereinafter jointly referred to as "metal ions") and each ligand of the plurality of multidentate ligand includes two or more carboxylates.

In some embodiments, at least one ligand of the plurality of multidentate ligand comprises an organic ligand which is at least bidentate and is selected from the group consisting of formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E, 4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4- carboxylic acid, pyridine-3-carboxylic acid, imidazole, 1H-benzimidazole, 2-methyl-1H-imidazole, and mixtures thereof.

Typically, the metal ion is selected from the group consisting of Group 1 through 16 metals of the IUPAC Periodic Table of the Elements including actinides, and lanthanides, and combinations thereof. Preferably, the metal ion is selected from the group consisting of $Li^+$, $Na^+$, $K^+$, $Rb^+$, $Cs^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{5+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $B^{3+}$, $B^{5+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$ and combinations thereof.

Typically, the cluster has formula $M_m X_n$ where M is the metal ion, X is selected from the group consisting of Group 13 through Group 17 anion, m is an number from 1 to 10, and n is a number selected to charge balance the cluster so that the cluster has a predetermined electric charge Preferably, X is selected from the group consisting of $O^{2-}$, $N^{3-}$ and $S^{2-}$. Preferably, M is selected from the group consisting of $Li^+$, $K^+$, $Na^+$, $Cs^+$, $Mg^{2+}$, $Ca^{2+}$, $Sr^{2+}$, $Ba^{2+}$, $V^{2+}$, $V^{3+}$, $V^{4+}$, $V^{5+}$, $Mn^{2+}$, $Re^{2+}$, $Fe^{2+}$, $Fe^3$, $Ru^{3+}$, $Ru^{2+}$, $Os^{2+}$, $Co^{2+}$, $Rh^{2+}$, $Ir^{2+}$, $Ni^{2+}$, $Pd^{2+}$, $Pt^{2+}$, $Cu^{2+}$, $Zn^{2+}$, $Cd^{2+}$, $Hg^{2+}$, $Si^{2+}$, $Ge^{2+}$, $Sn^{2+}$, and $Pb^{2+}$. More preferably M is $Zn^{2+}$ and X is $O^{2-}$.

Typically, the multidentate linking ligand has 6 or more atoms that are incorporated in aromatic rings or non-aromatic rings. Preferably, the multidentate linking ligand has 12 or more atoms that are incorporated in aromatic rings or non-aromatic rings. More preferably, the one or more multidentate linking ligands comprise a ligand selected from the group consisting of ligands having formulae 1 through 27:

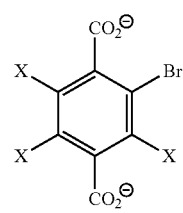

1

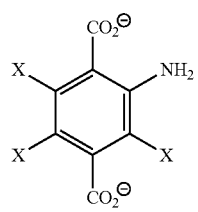

2

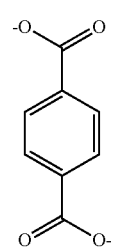

3

-continued

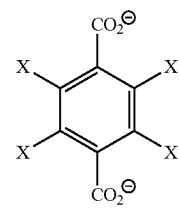

4

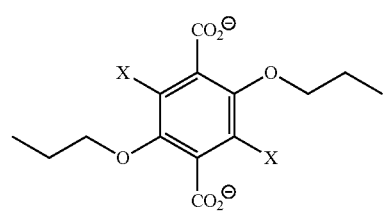

5

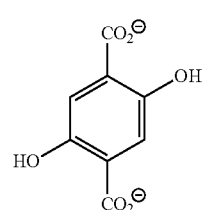

6

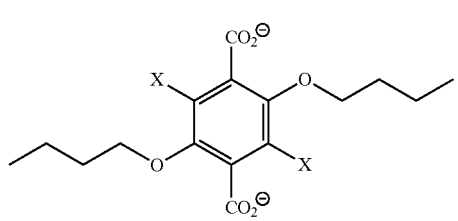

7

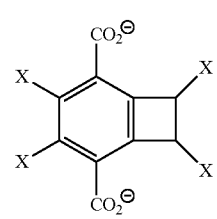

8

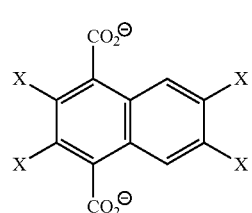

9

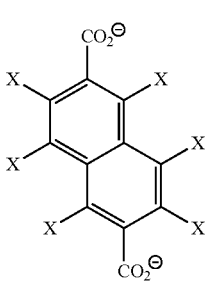

10

-continued
11
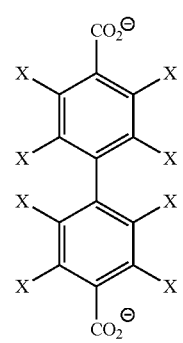
12
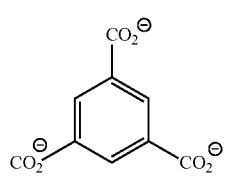
13
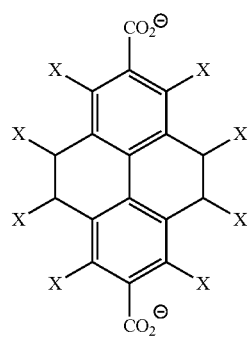
14
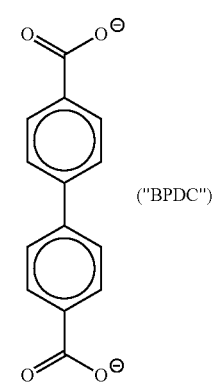
("BPDC")
-continued
15
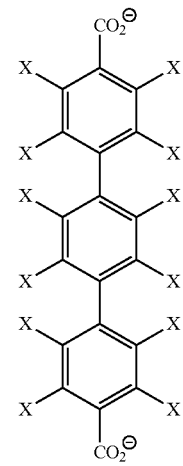
16
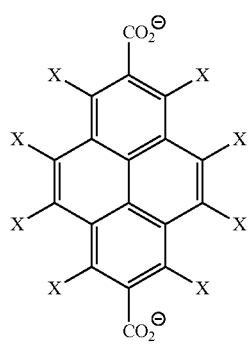
17
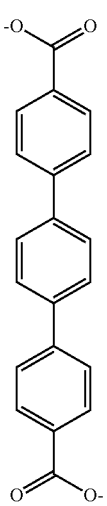
18
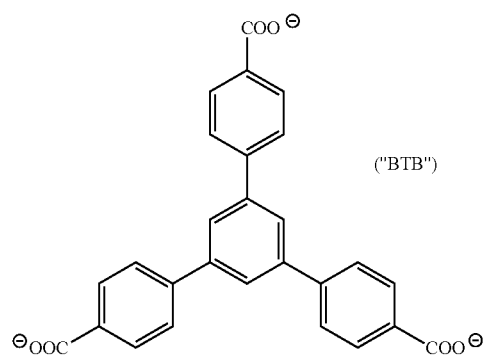
("BTB")

-continued
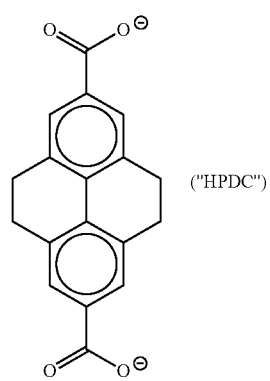
("HPDC")
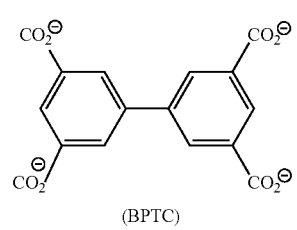
(BPTC)
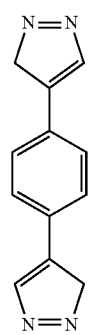
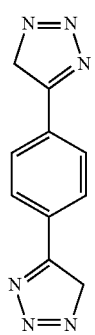
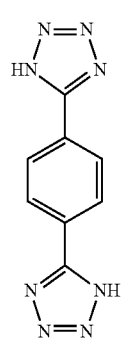
-continued
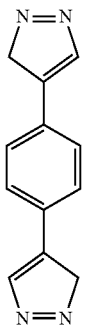
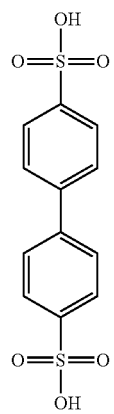
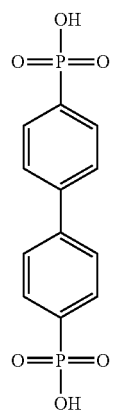
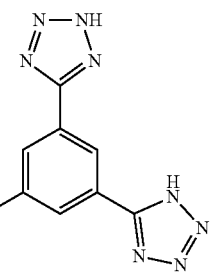
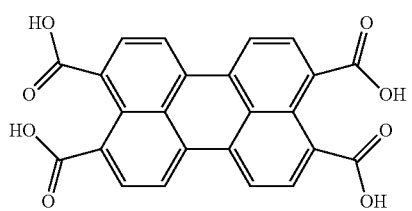

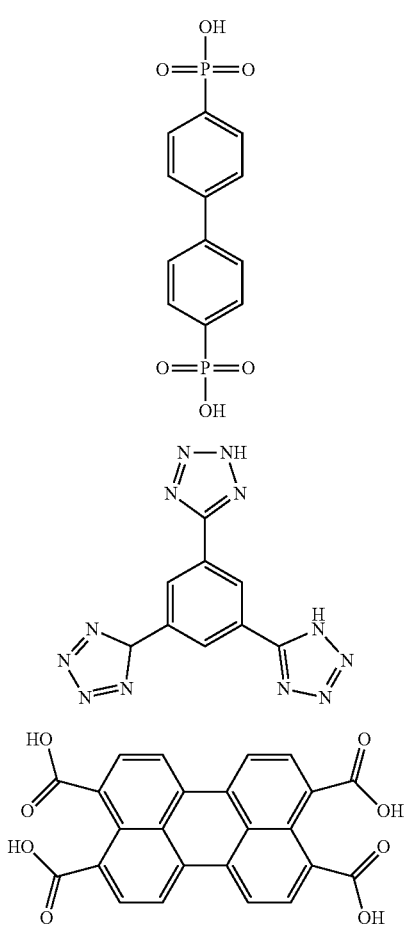

wherein X is hydrogen, —NHR, —N(R)$_2$, halides, $C_{1-10}$ alkyl, $C_{6-18}$ aryl, or $C_{6-18}$ aralkyl, —NH$_2$, alkenyl, alkynyl, —Oalkyl, —NH(aryl), cycloalkyl, cycloalkenyl, cycloalkynyl, —(CO)R, —(SO$_2$)R, —(CO$_2$)R—SH, —S(alkyl), —SO$_3$H, —SO$^{3-}$M$^+$, —COOH, —COO-M$^+$, —PO$_3$H$_2$—, —PO$_3$H-M$^+$, —PO$_3{}^{2-}$M$^{2+}$, or —PO$_3{}^{2-}$M$^{2+}$, —NO$_2$, —CO$_2$H, silyl derivatives; borane derivatives; and ferrocenes and other metallocenes; M is a metal atom, and R is $C_{1-10}$ alkyl.

In one embodiment, the multidentate linking ligand comprises a ligand having formula 3 previously described. In another embodiment, the multidentate linking ligand comprises a ligand having formula 18 ("BTB"). In a further embodiment, the multidentate linking ligand comprises a ligand having formula 14.

BRIEF DESCRIPTION OF THE DRAWINGS

The application file contains at least one drawing executed in color. Copies of this patent application publication with color drawings will be provided by the Office upon request and payment of the necessary fee. The present invention will now be described with reference to the figures of the accompanying drawings, which illustrate particular preferred embodiments of the present invention, wherein.

DETAILED DESCRIPTION

The present invention provides a new continuous flow chemistry apparatus, system and process for producing a large number of metal organic frameworks even when requiring a number of different reaction conditions.

The apparatus of the present invention comprises a tubular flow reactor comprising a tubular body into which, in use, precursor compounds which form the metal organic framework are fed and flow, said tubular body including at least one annular loop. In exemplary embodiments, the tubular body comprises a coil. The tubular flow reactor therefore comprises a coiled or coil tubular flow reactor.

The Inventors have found that the use of a coiled reactor enables more homogeneous heating and better mixing and as consequence higher quality materials and less reaction time in comparison to prior published studies of MOFs produced by continuous processes. It is also thought that coiling may assist in some embodiments in preventing clogging of the tubular reactor allowing for "continuous" use resulting in large scale production. The present invention therefore provides a fast, cost-effective environmentally friendly strategy to produce high-quality MOF materials at a large scale.

Advantageously, the process is capable for being scaled (more than 30-fold) without a loss in yield or surface area in the material with a control over particle size. The present invention can therefore permit large-scale production of MOFs at drastically reduced costs, allowing commercialisation of these MOFs for many potential real world applications. The present invention provides a fast, cost-effective environmentally friendly strategy to produce high-quality MOF materials at a large scale.

Figure 1A:
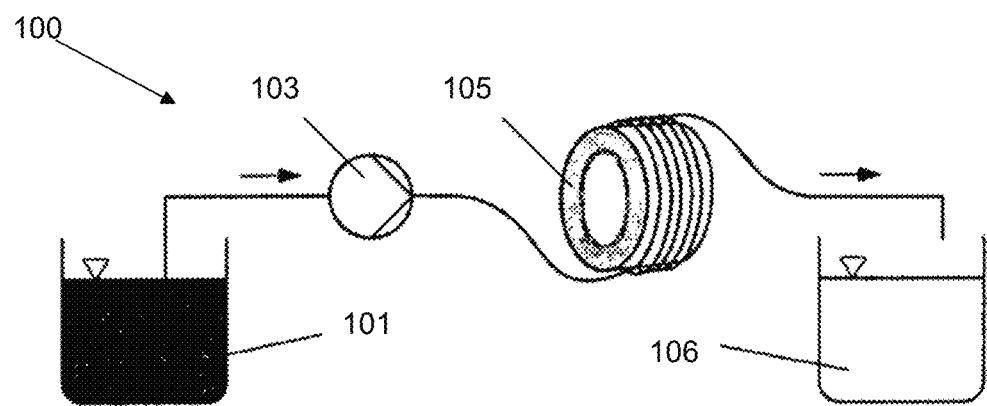
FIG. 1A provides a schematic representation showing the general flow reactor setup for the production of metal-organic framework solutions according to one embodiment of the present invention.

The flow reactor can have a large number of different process flow configurations:

FIG. 1A illustrates a first example flow diagram of a first continuous process 100 for producing MOF. In this process, a single feedstock tank 101 is used to feed a continuous flow reactor 105. The continuous flow reactor 105 comprises a coil reactor comprising a plurality of annular loops or turns centered about a centreline. Feedstock tank 101 includes a solution of MOF precursor compounds mixed together in solvent. This solution is then pumped 103 into the continuous flow reactor 105 to which heat is applied to induce reaction between the MOF precursor compounds. The produced MOF is collected in the product tank 106.

Figure 1B:
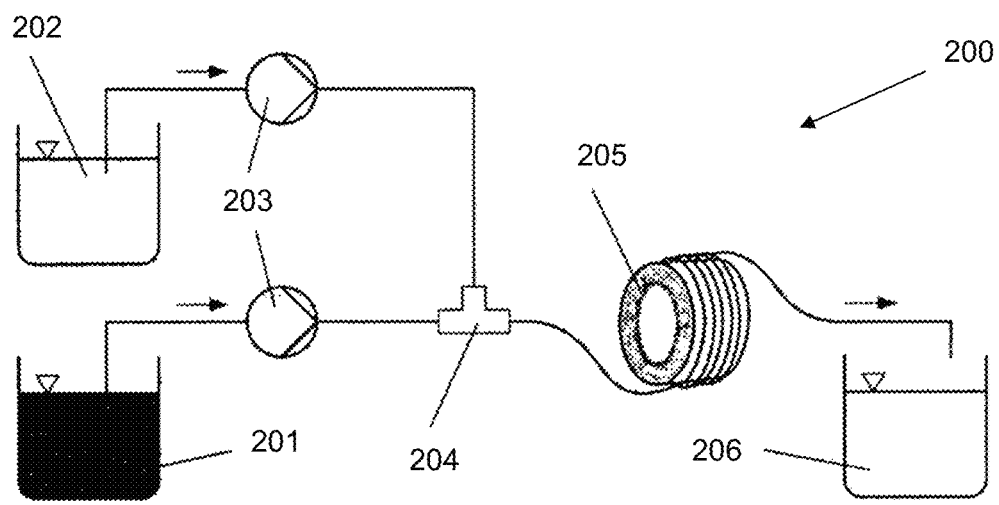
FIG. 1B provides a schematic representation showing the general flow reactor setup for the production of metal-organic framework solutions according to another embodiment of the present invention.

FIG. 1B illustrates a second example flow diagram of a second continuous process 200 for producing MOF. In this process, a first feedstock tank 201 includes a solution of a first precursor compound(s) in solvent. A second feedstock tank 202, includes a second precursor compound(s) in solvent. The solutions from each of the first and second feedstock tanks 201 and 202 are then pumped 203 to a T-piece mixer 204 (which in other embodiments could be Y- or cross junction mixer) where their flows are combined and passed through to continuous flow reactor 205. The continuous flow reactor 205 comprises a coil reactor comprising a plurality of annular loops or turns centered about a centreline. Heat is then applied to the reactor 205 to which heat is applied to induce reaction between the MOF precursor compounds. The produced MOF is collected in the product tank 206.

Figure 2A:
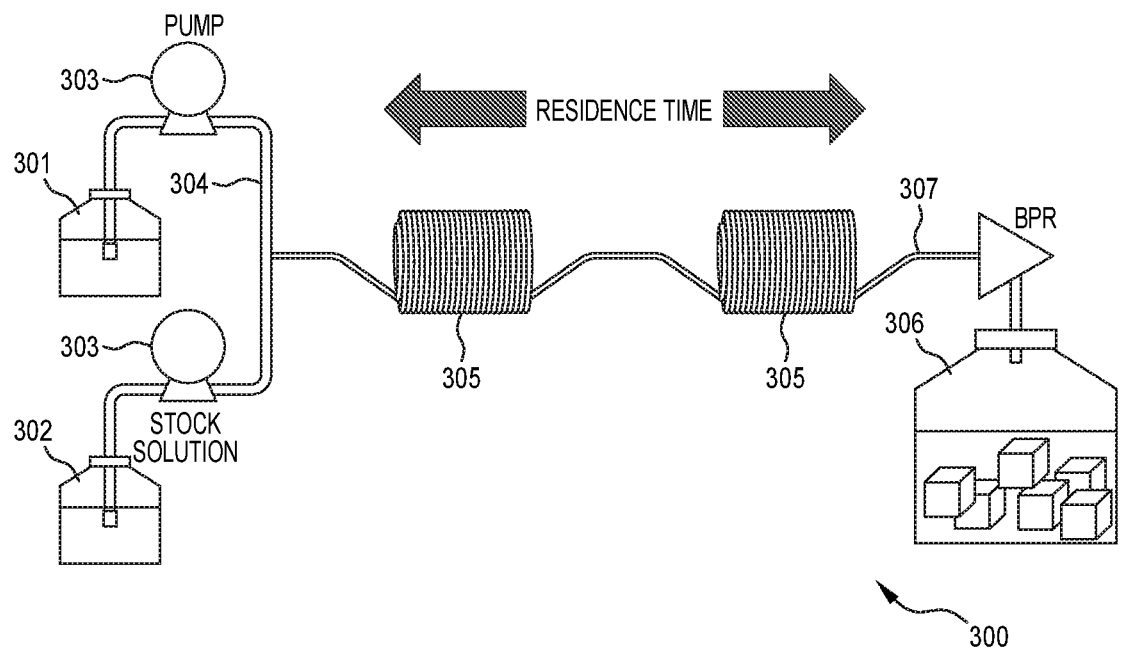
FIG. 2A provides a schematic representation showing the general flow reactor setup for the production of metal-organic framework solutions according to yet another embodiment of the present invention.

FIG. 2A illustrates a third example flow diagram of a third continuous process 300 for producing MOF. The flow diagram is similar to the flow diagram shown in FIG. 1B with the exception that the flow reactor 305 comprises two series connected coil reactors. Each continuous flow reactor 305 comprises a coil reactor comprising a plurality of annular loops or turns centered about a centreline. In this process, a first feedstock tank 301 includes a solution of a first precursor compound(s) in solvent. A second feedstock tank 302 includes a second precursor compound(s) in solvent. The solutions from each feedstock tanks 301 and 302 are then pumped 303 to the T-piece/mixer 304 where their flows are combined and passed through to continuous flow reactor 305. Heat is then applied to the reactor 305 to which heat is applied to induce reaction between the MOF precursor compounds. Reactor 305 comprises two coiled reactors fluidly liked in series. This arrangement increases the reactive length of the overall flow reactor 305. It should be appreciated that any number of coiled tubular reactors could be connected in series. The produced MOF is collected in the product tank 306.

In each of the systems shown in FIGS. 1A, 1B and 2A, the reaction solution is transferred via a flow line and introduced into the flow reactor 105, 205, 305. Introducing the reaction solution into the flow reactor 105, 205, 305 can be facilitated by any suitable means, but this will generally be by action of a pump 103, 203, 303. Those skilled in the art will be able to select a suitable pump 103, 203, 303 for the purpose of transferring the reaction solution from the vessel 101, 201, 202, 301, 302 along the flow line and introducing it to the flow reactor 105, 205, 305. The flow line is of a tubular type herein described and in effect forms the flow reactor 105, 205, 305 by being shaped into a coil configuration. The distinction between the flow line and the flow reactor 105, 205, 305 is that the flow reactor 105, 205, 305 is a designated section of the flow line where formation of the MOF from the precursor solutions is to be promoted. Promoting the formation of the MOF is shown by way of application of appropriate heat to the flow reactor 105, 205, 305. The coiled section of the flow line is then readily demarcated as the flow reactor 105, 205, 305.

It will be appreciated that the illustrated process can be operated continuously by ensuring that vessel 101, 201, 202, 301, 302 is maintained with reaction solution. Multiple flow lines can of course also be used to form the flow reactor 105, 205, 305 so as to increase the volume of reaction solution drawn from vessel 101, 201, 202, 301, 302 and thereby increase the volume of MOFs produced.

Figure 2B:
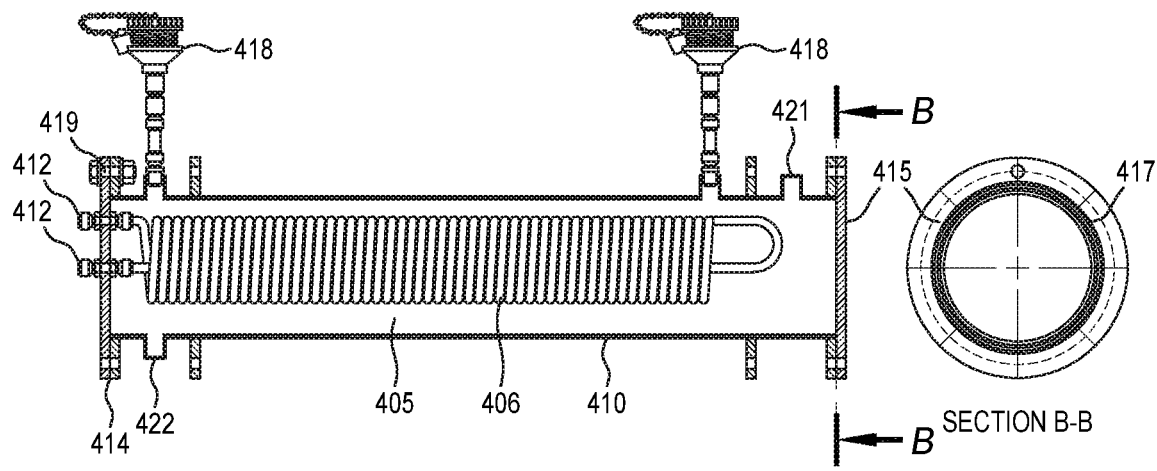
FIG. 2B provides a schematic representation showing one embodiment of the coil flow reactor setup for the production of metal-organic framework solutions according to yet another embodiment of the present invention.
Figure 2C:
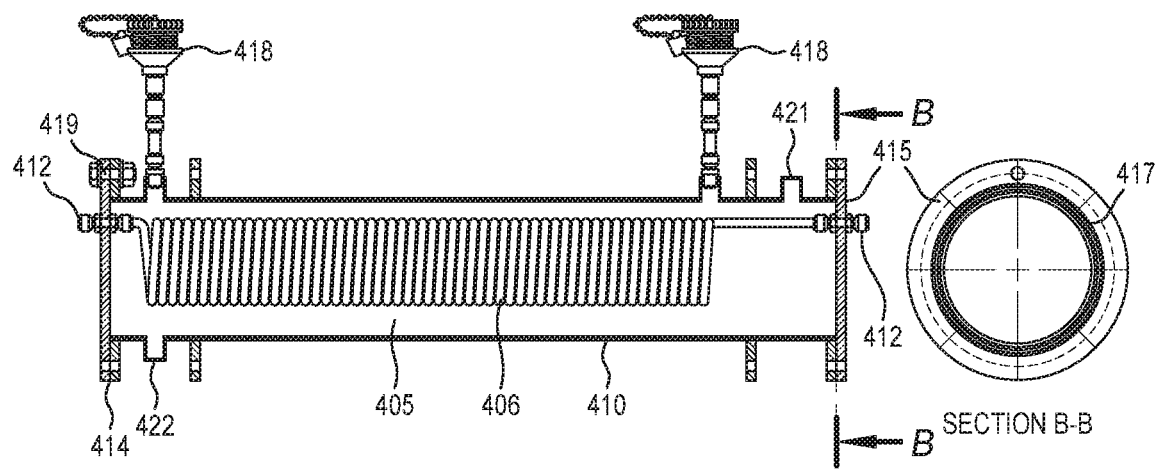
FIG. 2C provides a schematic representation showing another embodiment of the coil flow reactor setup for the production of metal-organic framework solutions according to yet another embodiment of the present invention.

FIGS. 2B and 2C shows particular embodiments of flow reactor 405 which can be used in the flow set up shown in FIGS. 1A, 1B and 2A. The embodiment of the flow reactor 405 shown in 2B comprises an elongate coil 406 including aligned inlet and outlet 412 housed within a tubular housing 410. The elongate coil 406 comprises a coil reactor comprising a plurality of annular loops or turns centered about a centreline (described in more detail below). The tubular housing is metallic, preferably stainless steel and includes two bulkhead ends 414, 415 which are sealed via o-rings 417 to the main body of the housing using bolts 419. In use, the MOF precursor fluid flows through the coil 406, whilst heating fluid passes through the housing 410. Temperature measurement of the contents on the shell side is via components 418. In this respect, the coil 406 and housing 410 is heated via heating inlet and outlet port connections 421 and 422 through which heated fluid, for example a heating gas such as nitrogen or heating fluid such as an oil or the like, are fed and extracted to heat the elongate coil 406. The coil 406 can have any suitable dimensions. In one embodiment, the coil is a 845 mm long coil of 0.25" stainless steel tubing having 90 turns of coil diameter ~7480 mm (outer diameter) with 3 mm spacing between each annular loop or turn. In another embodiment, the coil 406 is a 863 mm long coil of 0.5" stainless steel tubing having 56 turns of coil diameter ~130 mm with 3 mm spacing between each annular loop or turn. with coil diameter of 130 mm (outer diameter). It should be noted that the illustrated tubes are made from stainless steel. However, the choice of material is dependent on the chemistry of the MOF reaction, i.e. the metal salt, ligand and solvent used. Accordingly, plastics or other alloys may also be used. It is noted that insulation is included on the outside of the tubular housing 410 to limit heat loss.

The embodiment of the flow reactor 405 shown in FIG. 2C comprises a very similar set up to that shown in FIG. 2B with the exception that the inlet and outlet 412 of the elongate coil are on opposite ends of the housing 410. Due to these similarities, the same reference numerals have been used for this embodiment, and the above description in relation to the embodiment illustrated in FIG. 2B equally applies to the embodiment shown in FIG. 2C.

The apparatus, process and system of the present invention can further include a ultrasonic/megasonic separation apparatus that can separate a metal-organic framework (MOF) content from a solution. This separation apparatus has been found to purify the MOF, removing contaminants from the pores of the MOF and also improve the surface area of the treated MOF, producing a purified MOF having a higher surface area than comparable commercially available samples.

The Inventors have found that the use of ultrasonic and megasonic frequencies not only separates MOF material/particles from other components in a mother solution, but also purifies the separated MOF material. MOF material is extremely porous and therefore contaminant species in a solution can be trapped or otherwise located in these pores. This separation apparatus has been found to substantially remove contaminants from the pores of MOF material treated with this separation method and apparatus. This produces a desirable substantially pure MOF material which is highly saleable. The use of ultrasonic and megasonic frequencies has also been found to improve the surface area of the final product, acting as an alternate process to the time consuming and costly calcinations traditionally used for surface area improvement. The process can therefore assist in maintaining MOF product quality i.e. porosity, thermal and chemical stability.

Ultrasonic and/or megasonic separation according to the present invention applies >20 kHz, in some cases >400 kHz, preferably between 20 to 4 MHz, preferably 500 kHz to 2 MHz, more preferably between 800 kHz and 2 MHz, and yet more preferably between 1 MHz and 2 MHz high frequency ultrasound to create a standing wave, i.e. regions of minimal pressure (nodes) and maximal pressure (antinodes) within a liquid filled separation chamber. Whilst not wishing to be limited to any one theory, the Inventor's consider that when using this method, suspended particles or droplets migrate specifically towards one of these two regions due to acoustic radiation forces, based on their density and compressibility. In general, the aggregated MOFs are slightly denser than the surrounding fluid, and migrate towards the pressure nodes. This gathering of MOF material enhances the tendency to form larger aggregates which then sediment at a greatly accelerated rate to the bottom of the separation chamber, where they can be collected.

Ultrasonic and/or megasonic operation also has the ability to achieve specificity of separation based on particle size by tuning of the operation parameters such as frequency and energy density.

Ultrasonics and/or megasonic operation involves no moving parts, and can have a low surface area of contact with the fluid providing a lower capacity for fouling, and ease of cleaning. A separator according to the present invention essentially comprises a housing or container in which a liquid reservoir can be formed. The liquid reservoir is filled with the MOF containing solution produced by the tubular flow reactor of the present invention. A high frequency transducer, such as a plate transducer is either submerged in the liquid filled reservoir or engaged with a wall of reservoir to project ultrasonic and/or megasonic frequencies through the MOF containing solution for a certain length of time to effects the desired separation of MOF from solution and/or separation of contaminants from the MOF into the solution.

The Applicant considers that the size, material and/or geometry of the separation vessel or housing (which may, in some cases be housed within the tubular reactor) may have an effect on the outcome (degree, efficiency or the like) of the separation process of MOF. Similarly, the positioning, arrangement and alignment of transducers within a separation apparatus may have an effect on the outcome (degree, efficiency or the like) of separation process of MOF.

The Applicant notes that ultrasonics and megasonics are a well know separation technique for particles, particularly in the biotechnology and food processing areas. Previous applications of ultrasonics and megasonic involved liquid/liquid and solid/liquid separation especially in food processing (milk fat separation and palm oil separation). However, the Inventors are not aware of any previous published work using ultrasound, in particular megasonics, for the combined separation, washing, and/or activation of any porous material.

The inventors believe that the ultrasonic and megasonic ranges of the present invention provide at least one of surface area improvement, separation and/or washing properties for MOF containing solutions. The difference between ultrasonic and megasonics lies in the frequency that is used to generate the acoustic waves. Ultrasonic uses lower frequencies (20 to 400 kHz) and produces random cavitations. Megasonic uses higher frequencies frequency (>0.4 MHz to several MHz) and produces controlled and smaller cavitations which allows the separation of nanocrystals (in our case, the MOFs). Furthermore, higher megasonic frequencies do not cause the violent cavitation effects found with ultrasonic frequencies. This significantly reduces or eliminates cavitation erosion and the likelihood of surface damage to the product being cleaned.

EXAMPLES

The production of five studied MOF, copper trimesate (HKUST-1), zirconium terephthalate (UiO-66), scandium biphenyl-tetracarboxylate (NOTT-400), aluminium fumarate (Al-fum) and aluminium terephthalate (MIL-53) using process, system and apparatus according the present invention, will now be exemplified by example. However, it should be appreciated that the present invention is suitable for use with a large number of MOFs and should therefore not be limited to the exemplified MOF structures in these example. The examples provided can therefore be more generally applied to a wide range of MOFs.

Example 1—Synthesis of HKUST-1, UiO-66 and NOTT-400

To demonstrate the effectiveness and the versatility of this approach, three different families of MOFs have been synthesized: copper trimesate (HKUST-1), zirconium terephthalate (UiO-66) and scandium biphenyl-tetracarboxylate (NOTT-400). These three MOFs are thermally and chemically stable crystals which represent some of the most interesting materials for potential applications in gas storage and catalysis.

A schematic of the overall experimental apparatus is shown in FIG. 2A. The apparatus 300 and production method uses a commercially available flow chemistry synthesis platform (Vapourtec® R2+/R4 see below) to simultaneous pump separate precursor solutions of the organic ligand 301 and the metallic salt 302 into a T-micro mixer 304 via HPLC pumps 303. The mixed solvent streams were combined and directed into reactor 305 which comprised coiled flow reactors consisting of one to four (in this case one) 1.0 mm ID perfluoroalkoxy polymer (PFA) coil modules connected in series.

Experiments were performed using a commercially available continuous flow reactor Vapourtec R2+/R4 (www.vapourtec.co.uk) consisting of two PFA polymer tubular reactors used in a typical mesoscale synthesis of MOFs. The system comprises the pumping and reagent selection module (top stage) and the four channel air-circulated heating reactor coils (lower stage). In a typical synthesis of metal-organic frameworks, separate solutions of the precursors are directed into the reactor by HPLC pumps 303 through a T-type static mixer 304 to promote complete mixing of the separate reagent streams. The combined mixed reactants are then directed into the heated reactor zone of the Vapourtec R4 unit which comprises coiled tubular reactors 305 fabricated from perfluoroalkoxy polymer (PFA) tubing (internal diameter of 1 mm and a volume of 10 mL for each tubular reactor 305). Where required, the reactor volume can be readily increased by connecting the coiled reactor tubes in series (up to four coils for a single Vapourtec R4 unit). On exiting the reactor zone, the stream is passed through a back-pressure regulator 307 (Upchurch) (100 psi) to maintain constant the pressure of the flow stream. The exiting product stream was then collected into a volumetric flask 306 (100 mL) whereupon it was cooled to room temperature.

Each reactor coil 305 has a volume of 10 mL and its temperature is regulated to be constant and homogenous throughout the reaction, eliminating the possible temperature gradients often observed in batch reactors.

As noted below, the synthesis of HKUST-1 was performed in a total volume of 20 mL at 80° C. and at total flow rates of 2, 10 and 20 mL·min$^{-1}$, which resulted in a residence time of 10, 5 and 1 min respectively. UiO-66 was also successfully synthesized using the same set-up but at 130° C. in 10 min and using a flow rate of 2 mL·min$^{-1}$ and NOTT-400 at 85° C. in 15 min, at 2 mL·min$^{-1}$, using a total volume of 30 mL.

Synthesis of HKUST-1 Using Vapourtec R4/R21 Reactor

In a typical reaction, solutions of 0.1 M Cu(NO$_3$)$_2$·3H$_2$O and 0.24 M benzene-1,3,5-tricarboxylic acid (BTC) both in ethanol, were pumped into the flow reactor (PFA tubing, 20 mL). The synthesis was conducted at 80° C. using three total flow rates of 2, 10 and 20 mL·min$^{-1}$ giving a residence time of 10, 5 and 1 min respectively and at 140° C. using a flow rate of 20 mL·min$^{-1}$. The material was washed twice with ethanol and dried under vacuum for 8 hours at 40° C. Yield: 74% for 2 mL·min$^{-1}$ at 80° C.; 61% for 10 mL·min$^{-1}$ at 80° C.; 58% for 20 mL·min$^{-1}$ at 80° C.; 89% for 20 mL·min$^{-1}$ at 140° C.

Synthesis of UiO-66 Using Vapourtec R4/R21 Reactor

In a typical reaction, the two reactants were 0.1 M ZrCl$_4$ and 0.1 M 1,4-tricarboxylic acid (BDC), both of them prepared in dimethylformamide (DMF).

The total volume was 20 mL. The synthesis was conducted at 130° C. and with at combined flow rate of 2 mL·min$^{-1}$ yielding a residence time of 10 min. The material was washed once with DMF and immersed in methanol bath for 2 days. The final product was dried under vacuum for 8 hours at 40° C. The resulting yield was 67%.

Synthesis of NOTT-400 Using Vapourtec R4/R21 Reactor

In a typical reaction, 0.04 MSc(SO$_3$CF$_3$)$_3$ and a 0.08 M Biphenyl-3,39,5,59-tetracarboxylic acid (H4BPTC) were prepared in a mixture of DMF, tetrahydrofuran (THF) and water and were pumped continuously into the flow reactor. The total reactor volume was 30 mL. The synthesis was conducted at 85° C. and with an individual flow rate of 1 mL·min$^{-1}$ giving a residence time of 15 min. The material was washed once with DMF and immersed in acetone bath for 1 day. The final product was dried under vacuum for 8 hours at 40° C. The resulting yield was 61%.

Characterisation

Scanning electron microscopy (SEM) images were collected on a Quanta 400 FEG ESEM (FEI) at acceleration voltage of 0.2-30 kV. Copper was used as support. The X-ray powder diffraction (XRPD) measurements were performed with an X'Pert Pro MPD diffractometer (Panalytical) over a 2θ range of 5° to 45°. The thermogravimetric analysis (TGA) was performed on a Perkin-Elmer STA-600 under a constant flow of N$_2$ at a temperature increase rate of 5° C./min. Gas adsorption isotherms for pressures in the range 0-120 kPa were measured by a volumetric approach using a Micrometrics ASAP 2420 instrument. All the samples were transferred to pre-dried and weighed analysis tubes and sealed with Transcal stoppers. HKUST-1, UiO-66 and NOTT-400 were evacuated and activated under dynamic vacuum at 1026 Torr at 140° C. for 8 hours, 120° C. for 12 hours and 170° C. for 12 hours respectively. Ultra-high purity N$_2$ and H$_2$ gases were used for the experiments. N$_2$ and H$_2$ adsorption and desorption measurements were conducted at 77 K. Surface area measurements were performed on N$_2$ isotherms at 77 K using the Brunauer-Emmer-Teller (BET) model with adsorption values increasing range of 0.005 to 0.2 relative pressures. In order to estimate the particle size of the MOFs a statistical study was done based on five different SEM images of each MOFs.

Results

Conventional batch synthesis requires between 24 h for the production of HKUST-1 and UiO-66 and 72 h for NOTT-400. The reaction times using the continuos flow reactors are therefore an improvement over the batch synthesis results. These short reaction times are made possible by the high surface-area-to-volume ratio in the reactor which is much higher than that of a typical bottom flask used in solvothermal synthesis. The dimensions of the flow reactor (1 mm ID) ensure an excellent heat and mass transfer showing a narrow residence time distribution and a near plug-flow like profile.

The hourly rate of MOF production of the synthesis was calculated to evaluate the impact of the continuos flow approach on larger scale production. The results are provided in Table 1, which provides the results of the present invention compared to other candidates for larger scale production of MOFs and commercially produced HKUST-1 sourced from the listed literature sources.

TABLE 1

Comparisons of the reaction time between MOFs synthesized by convectional batch and by flow chemistry. BET surface areas, grams of MOF produced per 1 hour using flow chemistry and space time yield (STY).

| MOF | Reaction time | SABET (m$^2$g$^{-1}$) | g · h$^{-1}$ | STY (kg m$^{-3}$d$^{-1}$)$^f$ |
|---|---|---|---|---|
| HKUST-1$^a$ | 1 min | 1852 | 1.48 | 592 |
| HKUST-1$^b$ | 5 min | 1673 | 2.04 | n/a |
| Basolite C300$^b$ | 150 min | 1820 | n/a | 225 |
| UiO-66$^a$ | 10 min | 1186 | 1.68 | 672 |
| UiO-66$^d$ | 24 h | 1147 | n/a | n/a |

TABLE 1-continued

Comparisons of the reaction time between MOFs synthesized by convectional batch and by flow chemistry. BET surface areas, grams of MOF produced per 1 hour using flow chemistry and space time yield (STY).

| MOF | Reaction time | SABET ($m^2g^{-1}$) | $g \cdot h^{-1}$ | STY ($kg\ m^{-3}d^{-1}$)[f] |
|---|---|---|---|---|
| NOTT-400[a] | 15 min | 1078 | 2.78 | 741 |
| NOTT-400[e] | 72 h | 1350 | n/a | n/a |

[a] Vapourtec Flow chemistry reactor (Mesoscale).
[b] Data from ref. Faustini, M. et al. Microfluidic Approach toward Continuous and Ultra-Fast Synthesis of Metal-Organic Framework Crystals and Hetero-Structures in Confined Microdroplets. J. Am. Chem. Soc. 135,14619-14626 (2013).
[c] Data from ref. Mueller, U. et al. Metal-organic frameworks-prospective industrial applications. J. Mater. Chem. 16, 626-636 (2006).
[d] Data from ref. Cavka, J. H. et al. A New Zirconium Inorganic Building Brick Forming Metal Organic Frameworks with Exceptional Stability. J. Am. Chem. Soc. 130,13850-13851 (2008).
[e] Data from ref. Ibarra, I. A. et al. Highly porous and robust scandium-based metal-organic frameworks for hydrogen storage. Chem. Commun. 47, 8304 (2011).
[f] Space-time yields given in this table based on the volume of the reaction mixture in 8 hours.

The reaction rate values obtained by a flow chemistry approach of the present invention are many multiples higher than any other values reported in the literature. This fact underlines the great potential of continuous flow processing for industrial production of MOF materials, especially bearing in mind that the setup allows to continuously produce material for extended periods of time without observable blocking of the reactor coil or back-pressure regulator.

Figure 3:
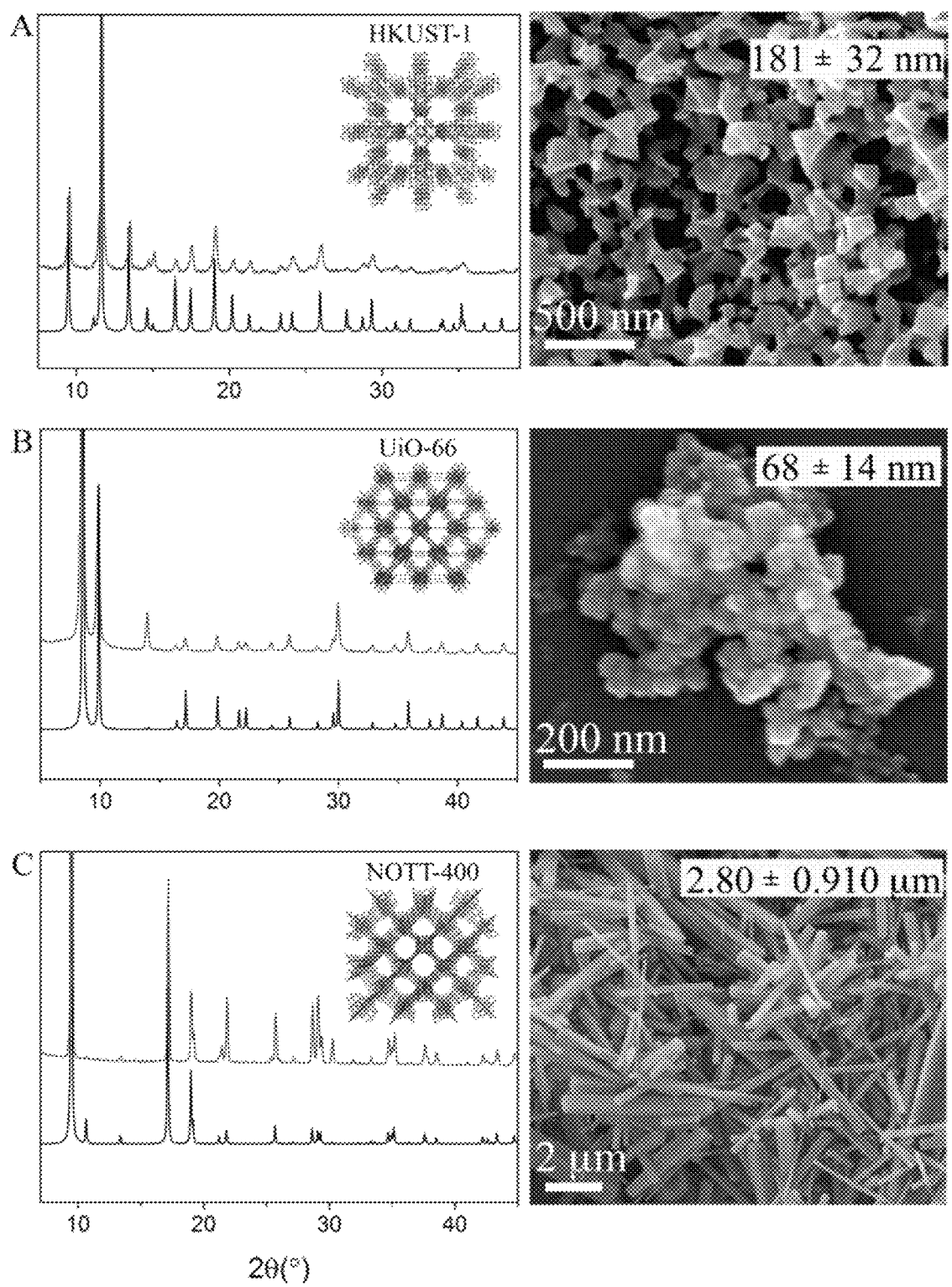
FIG. 3 provides characterization data of a) HKUST-1, b) UiO-66 and c) NOTT-400 crystals obtained by flow chemistry using a total flow rate of 2 mL·min$^{-1}$ respectively. Comparisons of the XRPD patterns obtained by flow (green) with simulated structures (black). SEM images of the crystals obtained by flow chemistry.
Figure 6:
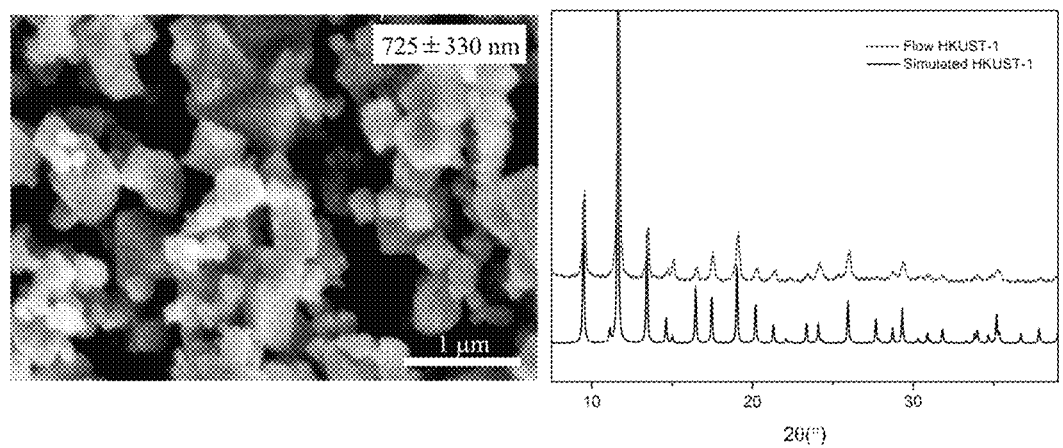
FIG. 6 provides SEM image and XRPD patterns of the HKUST-1 crystals synthesized by flow chemistry at 140° C. and using a flow rate of 20 mL·min$^{-1}$ (green), compared with the simulated XRPD pattern of HKUST-1 (black). This XRPD pattern was collected using Cu Kα radiation.

The overall quality of the produced HKUST-1, UiO-66 and NOTT-400 crystals was confirmed using X-Ray powder diffraction (XRPD). The diffraction patterns shown in FIG. 3 confirm that the purity of the crystals obtained by flow chemistry is identical to the crystals synthesized by conventional solvothermal methods. The thermogravimetric analysis (TGA) curves show a continuous weight loss over the temperatures ranges 50 to 100° C. due to the solvent loss, with small differences due to the type of solvent used in the purification processes. The size and morphology of the crystals were corroborated by scanning electron microscopy (SEM), as shown in FIGS. 3 and 6.

Figure 4:
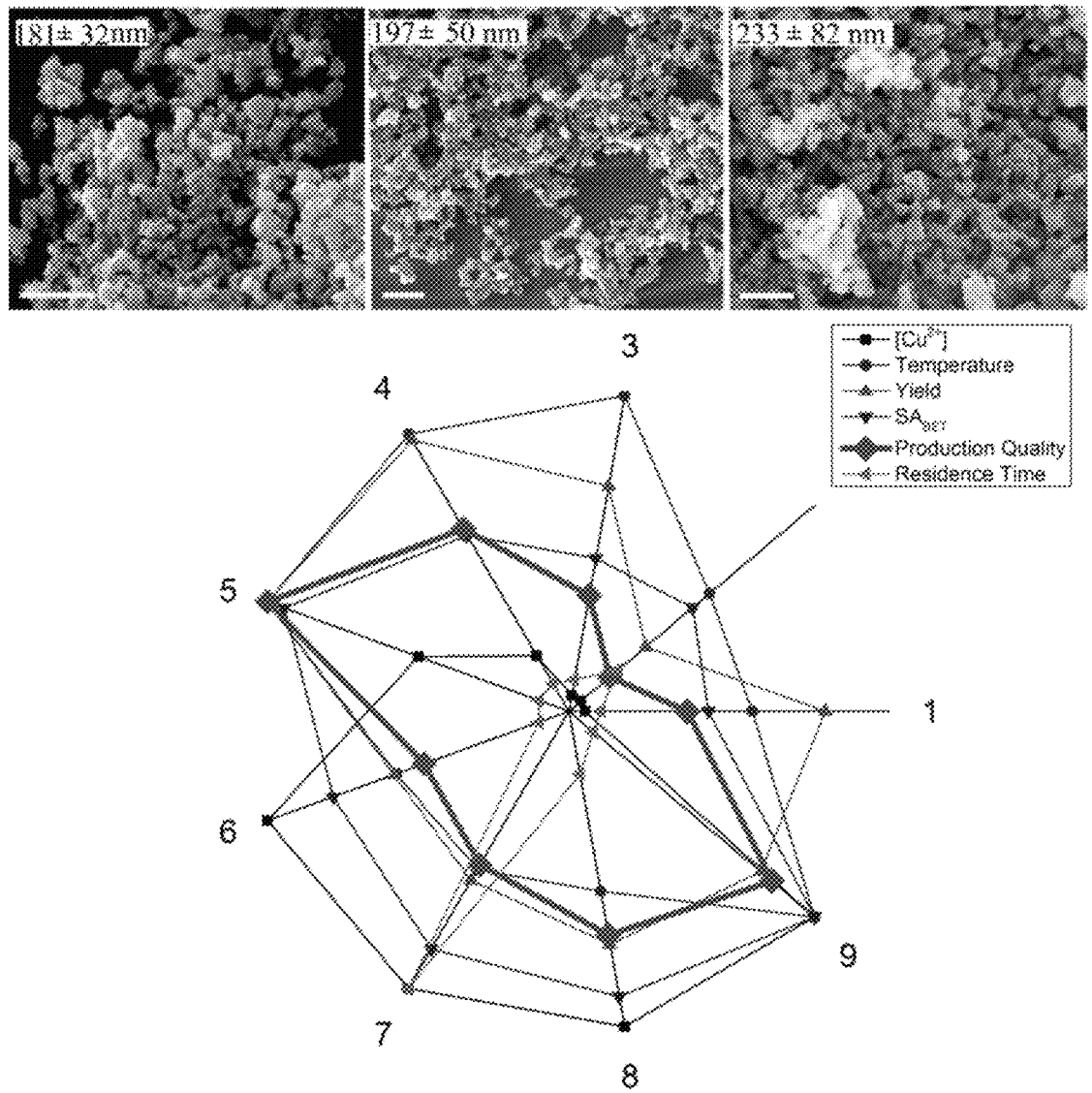
FIG. 4 provides representative SEM images of the HKUST-1 crystals synthesized by flow chemistry at 806° C. after 1, 2 and 10 minute residence times showing control over particle size (top). Scale bar: 500 nm. Overview diagram of the influence of reaction parameters on product synthesised based on data presented in the table (bottom). Production quality is defined as the product of BET surface area and percentage yield. Data have been normalised such that the maximum value for each parameter is set to unity.

The typical octahedral HKUST-1 crystals are obtained using different residence times and temperatures, where lower flow rates yielded more ideal crystal shapes (see FIG. 4). For UiO-66, small crystals under 100 nm are obtained, while for NOTT-400 rectangular crystals below 10 mm are obtained. These crystal sizes, as with other faster synthetic methodologies like microwaves, are smaller than the crystals obtained under standard solvothermal conditions. This effect is attributed to the rapid crystallization kinetics induced by the flow chemistry approach. Standard $N_2$ and $H_2$ adsorption measurements proved the porous character of the MOFs and yielded BET (Brunauer, Emmett and Teller) surface areas that are similar to values obtained by conventional methods, some mesoporosity was witnessed in UiO-66 due to inter-particle packing between the nano-sized crystallites.

The continuous flow chemistry set-up employed in the present case is amenable to precise control over reaction parameters. Taking advantage of this, a detailed investigation of different reaction conditions was undertaken to elucidate to what point facile and commercially attractive conditions (i.e. low temperatures, high concentrations, short residence times) could be employed prior to a loss of production quality, which in FIG. 4 is defined as the result of yield multiplied by surface area, normalised to a value between zero and one. Control of particle size is also attractive for tailoring MOF production to a specific application, without the need for bespoke equipment. For example, use in mixed matrix membranes requires nanoparticulate materials, whereas bulk applications such as gas storage are better suited to macroscale particles that are not flocculent.

Figure 5:
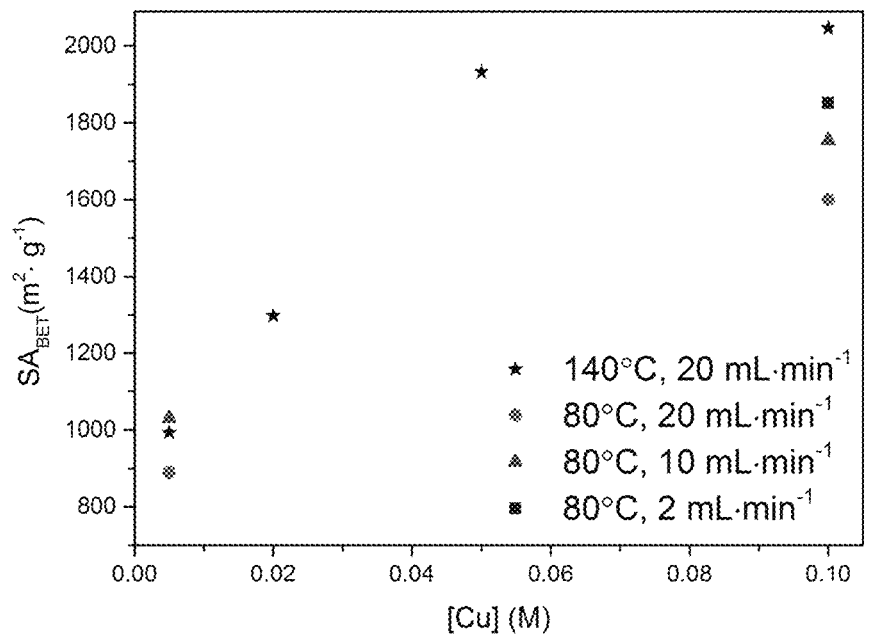
FIG. 5 provides representations of BET surface area, SA$_{BET}$, with respect to the different concentrations of copper used for the synthesis of HKUST-1 at 80° C. (a) and at 140° C. (b), using different flow rates.

The results indicate (FIGS. 4, 5 and 6) that reaction temperature is the key factor affecting product quality, with both yield and surface area correlated in this case. Higher copper concentrations moderate the yield, but surface areas were largely unaffected. Encouragingly, reducing residence time appeared to improve surface areas without diminishing yields. In this case, the increase in surface area could be accounted for by a corresponding decrease in particle size (FIG. 4, top). This type of control over particle size distribution from 100 nm to 100 μm is of paramount importance for many applications, such as adsorption and catalysis.

The continuous reaction apparatus of the present invention therefore led to the rapid production of three separate MOFs, namely HKUST-1, UiO-66 and NOTT-400. This can be achieved without loss in product quality, with process optimisation leading to unprecedented production efficiency as measured by space-time yields, and control over particle size without a loss of surface area or yield.

Example 4—MOF Synthesis and Megasonic Separation

Aluminium fumarate (Al-fum) and aluminium terephthalate (MIL-53) were synthesized using flow chemistry technology following the methodology outlined in Example 1.

A schematic representation showing the general flow reactor setup used in this example is shown and described above in relation to FIG. 2A. The reactor 405 used in this setup is shown in FIG. 2B, and has been described in detail above.

Here after mixing in T-mixer 304, the organic ligand and metal ions in solution with a solvent, preferably water and/or mixture of water and ethanol, at temperature from about 25° C. to about 130° C. (depending of the MOF synthesis) are then directed into a heated tubular flow reactor 305 (FIG. 2A) and 405 (FIG. 2B). The specific coil flow reactor 405 (FIG. 2B) used in this application had a 108 mL capacity with 6.0 mm ID stainless steel tube with a total flow rate of 90 mL $min^{-1}$. A MOF stream is obtained from the flow reactor 405/305 and is cooled to room temperature using a water bath heat exchanger.

It is noted that higher ligand concentration increase yields, however, increase also the risk of blockage in the flow reactor 405/305.

A MOF stream is obtained and is cooled to room temperature using a water bath heat exchanger (not illustrated). If desired, the solvent can be reused by recycling after the first separation stage. This is particularly attractive for recycling the unreacted ligand which is usually the most expensive reactant, or when an expensive or toxic solvent is used.

Wash and separation stages (again not illustrated) are performed preferably with water and/or with mixture of water and ethanol. A portion of the washing medium can be recycled back to the reactor 305/405, while the remaining liquid is sent to waste. Depending on the reaction conditions the recycle and waste streams consist of solvent, unreacted ligand and salt, as well as a reaction byproduct. The byproduct concentration depends on the recycle flow rate. Note that high concentrations may have a detrimental effect on the MOF synthesis reducing the yield, dictating the maximum feasible recycle flow rate.

The MOF crystals formed in Example 4 were isolated from the solvent using a megasonic apparatus and process according to one embodiment of the present invention. A conventional centrifuge was used as a control reference.

The megasonic separator 500 is shown in FIG. 7. The megasonic separator 500 applies >400 kHz high frequency ultrasound to create a standing wave, i.e. regions of minimal pressure (nodes) and maximal pressure (antinodes) within a separation chamber 510 of megasonic separator 500.

Figure 7A:
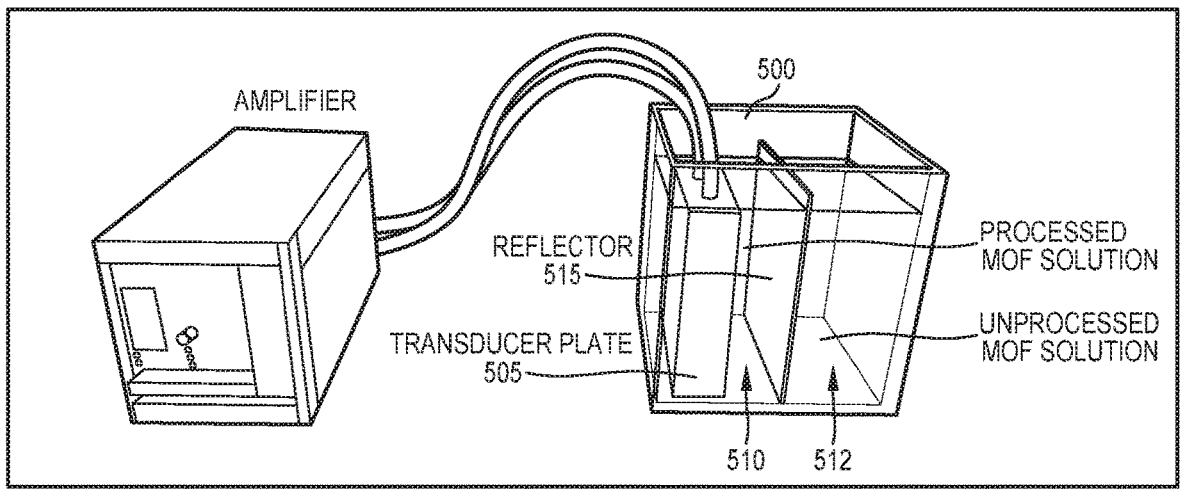
FIG. 7 provides a) a photograph of the ultrasonic/megasonic separator set-up with a high frequency system; b) a photograph of one 200 kHz plate transducer used in the reactor set up shown in (a); and c) a schematic of a standing wave pattern formed by the superimposition of a reflected sound wave within the separator shown in (a).
Figure 7B:
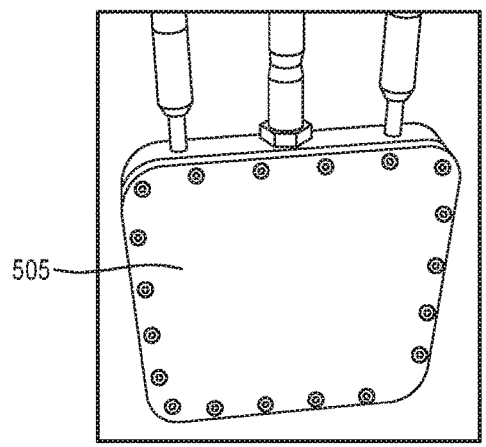

FIG. 7(a) shows the megasonic separator 500 set-up with a high frequency system using one 200 kHz plate transducer 505 (best shown in FIG. 7(b)). The megasonic separator 500 essentially comprises a 1.1 L stainless steel container. It should be noted that a clear polycarbonate 6-litre container shown in the Figures was used initially to visualize the separation process. However, normal operation and experiments were performed in a 1.1-litre stainless steel container (not pictured).

The illustrated clear polycarbonate 6-litre container is split into two sections, a 1.1 L treatment section 510 containing the transducer plate 505 and an unprocessed section 512. The treatment section 510 and unprocessed section 512 are separated by a metallic (stainless steel) reflector plate 515 used to reflect the megasonic waves.

The plate transducer 505 was used for sonication at a frequency of 2 MHz (305 W) for 10 min.

Figure 7C:
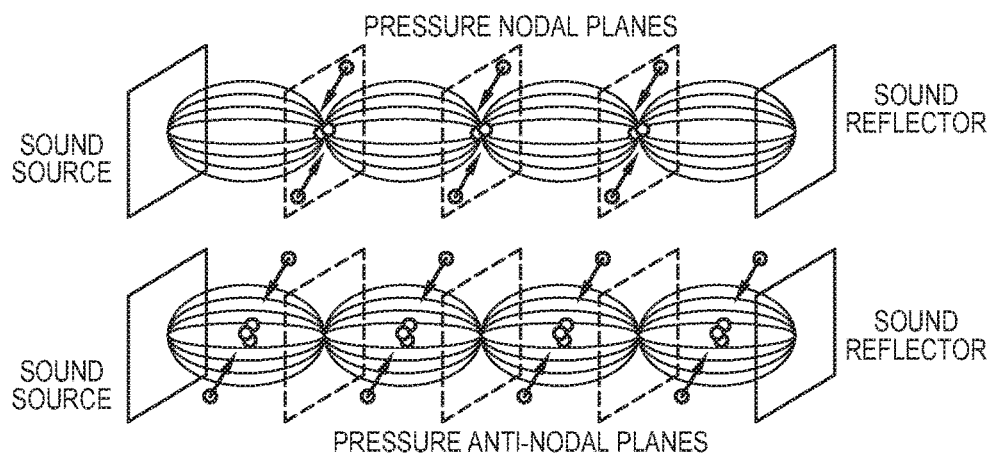
Figure 8:
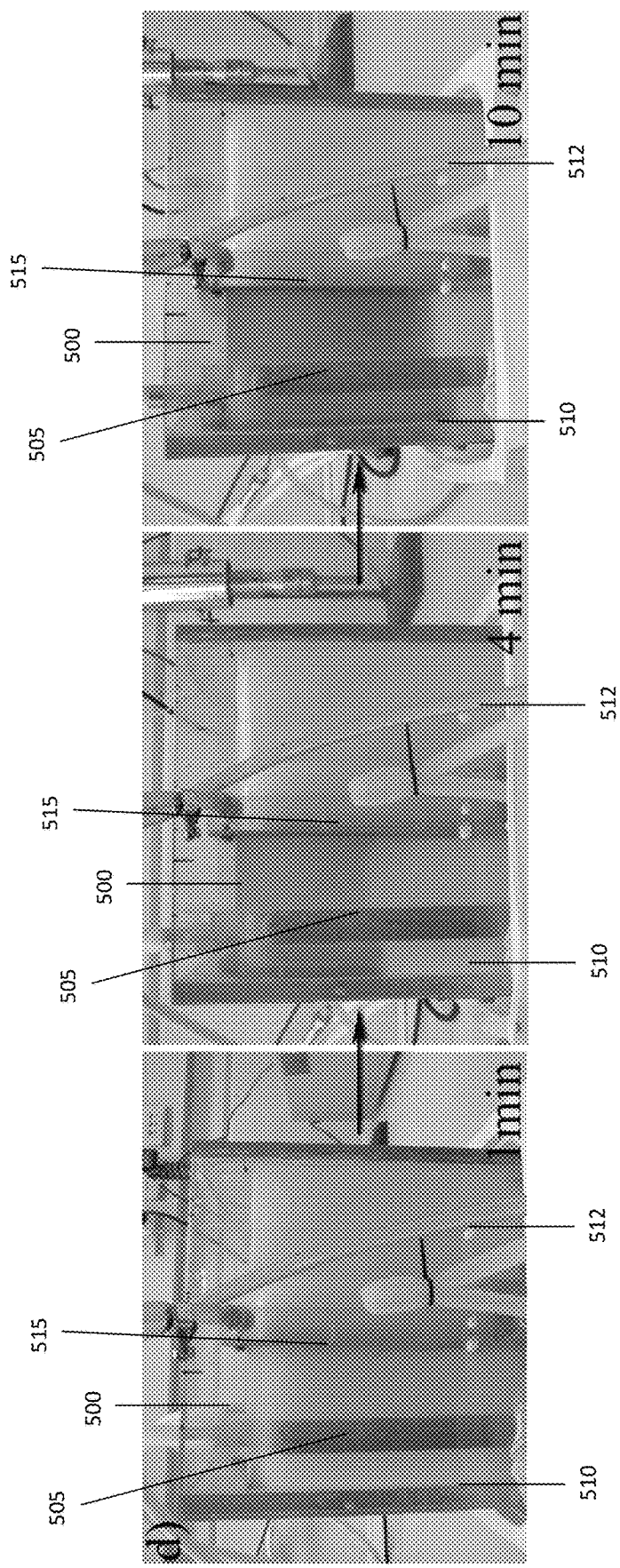
FIG. 8 provides three photographs of solution being treated in a separator shown in FIG. 7 at specific times (1 minute, 4 minutes and 10 minutes) during a separation process according to one embodiment of the present invention.

FIG. 7c shows the schematic of the standing wave pattern formed by the superimposition of a reflected sound wave within the treatment section 510. The separation distance between adjacent nodes or antinodes, is half a wavelength. Depending on the specific density and compressibility of the particles, they will collect either in the nodal (top, black dotted planes) as for the bright yellow particles or antinodal (bottom, red dotted planes) pressure planes as for the darker yellow particles. As previously noted, suspended particles or droplets migrate specifically towards one of these two regions due to acoustic radiation forces, based on their density and compressibility. In general, the aggregated MOFs are slightly denser than the surrounding fluid, and migrate towards the pressure nodes. As shown in FIG. 8, this gathering of MOF material enhances the tendency to form larger aggregates which then sediment settles at a greatly accelerated rate to the bottom of the separation chamber, where they can be collected.

FIG. 8 provides three photographs of a MOF solution being treated in a megasonic treatment apparatus 500 shown in FIG. 8(a) at specific times (1 minute, 4 minute and 10 minutes) during the megasonic separation process described above. In the left or separation compartment 510, the megasonic separation and purification process of the Al-MOF is shown. The right compartment 512 shows the same MOF solution without sonication. The settling of the MOF is clearly visible in the separation compartment 510 after 4 mins and 10 mins compared to the cloudiness of the same MOF solution without sonication shown in the right compartment 512.

Example 5—Investigation into Changes in MOF Composition

In order to investigate whether megasonics separation introduces changes in the MOF composition, ζ-potential measurements were recorded after each washing step of Example 5 as shown Table 2.

TABLE 2

ζ- Potential of the Al-Fumarate and MIL-53 MOF material after each wash step using Megasonics using water as a dispersant.

| MOF washing process (Megasonics) | ζ- potential (mV) |
| --- | --- |
| Al-Fumarate flow reactor | +8.3 ± 0.4 |
| Al-Fumarate wash 1 in $H_2O$ | +8.8 ± 0.0 |
| Al-Fumarate wash 2 in $H_2O$ | +8.8 ± 0.1 |
| Al-Fumarate wash 3 in $H_2O$ | +8.9 ± 0.2 |
| Al-Fumarate wash 4 in EtOH | +10.6 ± 0.2 |
| Al-Fumarate wash 5 in EtOH | +11.3 ± 0.8 |
| MIL-53 flow reactor | +13.3 ± 0.4 |
| MIL-53 wash 1 in $H_2O$ | +15.1 ± 0.5 |
| MIL-53 wash 2 in $H_2O$ | +14.7 ± 0.3 |
| MIL-53 wash 3 in $H_2O$ | +12.6 ± 0.5 |
| MIL-53 wash 4 in EtOH | +12.7 ± 0.2 |
| MIL-53 wash 5 in EtOH | +14.6 ± 0.1 |

No significant changes to the surface charge were observed, pointing to a separation that is based on reversible aggregation.

To determine the quality of the crystals, XRPD and SEM measurements of the MOFs separated with megasonics and by the standard lab-scale centrifuge were compared. X-Ray powder diffraction (XRPD) confirmed the crystallinity of our Al-fum and MIL-53, showing identical patterns to those of crystals synthesized by solvothermal methods. It was observed by scanning electron microscope that the high-frequency treatment also does not affect the size and shape distribution of the MOFs.

Figure 9:
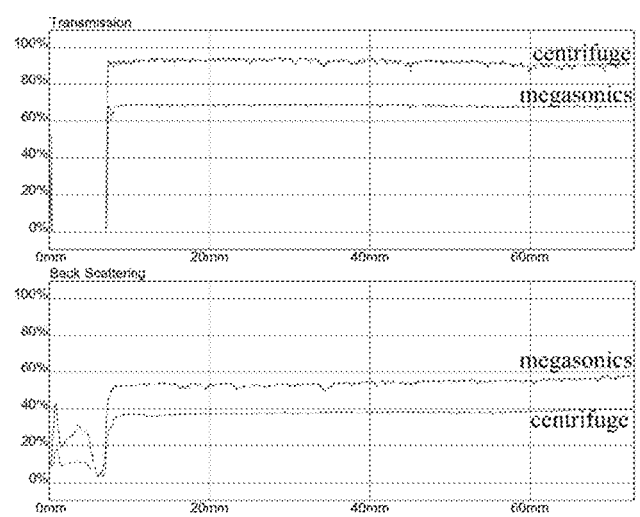
FIG. 9 provides a photographic comparison and a comparison plot of the backscattering and transmission data of the supernatant collected from the first separation of the MOF solution using centrifuge and ultrasonic/megasonic separator for (A) Al-Fumarate supernatant; and (B) MIL-53 (Al) supernatant.
Figure 9:
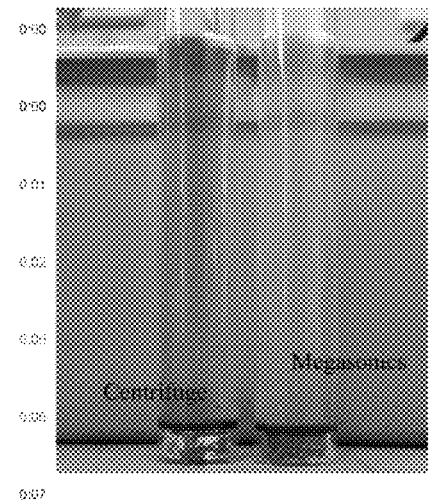
Figure 9:
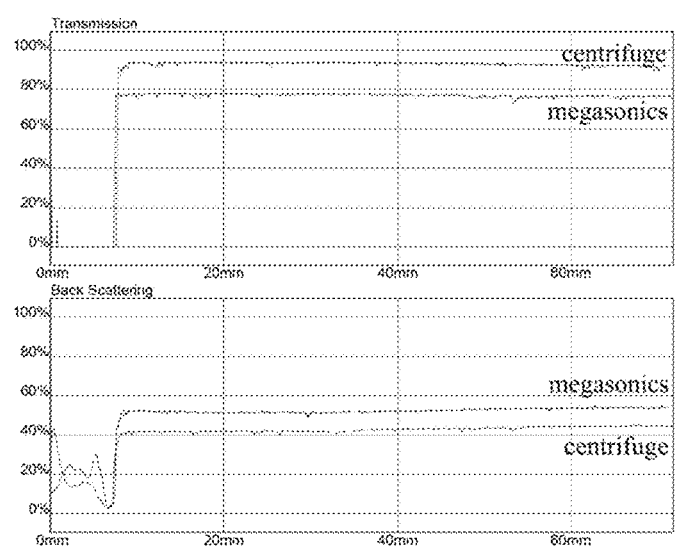
Figure 9:
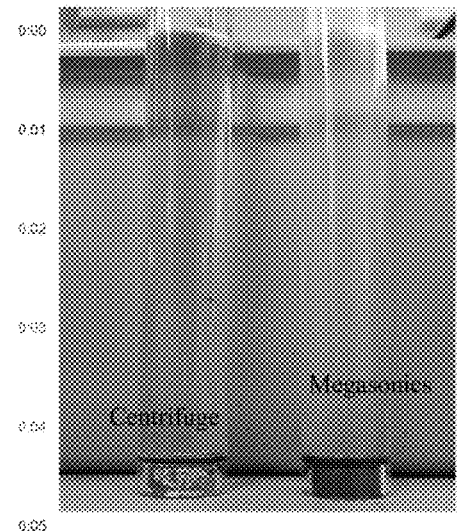

A comparison of the backscattering and transmission data of the supernatant collected from the first separation of the MOF solution using centrifuge and megasonics was undertaken as shown in FIG. 9. As shown in FIG. 9, the recoverable MOF yield obtained with megasonic separation compared to the conventional centrifuge method is 3% less for each washing step. This difference can be attributed to the fact that centrifuge separation generates a higher G-force compared to the settling by gravity in megasonics, which leads to a more effective removal of the MOF material.

The measurements of the BET surface areas revealed that the MOFs separated and washed with megasonics showed a drastic increase of 21% for the Al-Fum and 47% for MIL-53 over standard centrifuge washed MOF, which had BET values similar to literature (see Table 3).

TABLE 3

Comparisons of the reaction time between MOFs synthesized by convectional batch (using water as a reaction solvent) and by flow chemistry. BET surface areas, grams of MOF produced per 1 hour using flow chemistry and STY. Full adsorption isotherms are provided in the supplement information.

| | Reaction time | $g\ h^{-1}$ | Yield (%) | STY (kg · $m^3 \cdot d^{-1}$) | $SA_{BET}$ ($m^2\ g^{-1}$) |
| --- | --- | --- | --- | --- | --- |
| From reactor | | | | | |
| Al-fum | 1.2 min | 338.04 | 109.0 | 25,040 | — |
| MIL-53 | 1.2 min | 50.68 | 112.8 | 3,754 | — |
| Centrifuge × 5 | | | | | |
| Al-fum | 1.2 min | 281.88 | 90.9 | 20,880 | 890 |
| MIL-53 | 1.2 min | 42.14 | 93.8 | 3,121 | 806 |
| Megasonics × 5 | | | | | |
| Al-fum | 1.2 min | 225.07 | 72.6 | 16,672 | 1075 |
| MIL-53 | 1.2 min | 35.10 | 78.1 | 2,600 | 1183 |

TABLE 3-continued

Comparisons of the reaction time between MOFs synthesized by convectional batch (using water as a reaction solvent) and by flow chemistry. BET surface areas, grams of MOF produced per 1 hour using flow chemistry and STY. Full adsorption isotherms are provided in the supplement information.

|  | Reaction time | g h$^{-1}$ | Yield (%) | STY (kg · m$^3$ · d$^{-1}$) | SA$_{BET}$ (m$^2$ g$^{-1}$) |
|---|---|---|---|---|---|
| Commercial[a] |  |  |  |  |  |
| Al-fum Literature[b] | 10.2 min | 174 | 86 | 5339 | 1140 |
| MIL-53 | 4 hours | 125 | 86 | 1300 | 1010 |

[a]M. Gaab, N. Trukhan, S. Maurer, R. Gummaraju and U. Müller, *Microporous Mesoporous Mater.*, 2012, 157, 131-136.
[b]P. A. Bayliss, I. A. Ibarra, E. Pérez, S. Yang, C. C. Tang, M. Poliakoff and M. Schröder, *Green Chem.*, 2014, 16, 3796.

The Inventors attribute this improvement to the enhanced mass transfer that arises from acoustic streaming during megasonic application that promotes the removal of the excess organic ligands molecules inside of the pores. This is an important step forward for cost-effective and green production of MOFs as similar surface areas have only been obtained using laboratory scale methods that would be expensive at large scale, namely by using supercritical ethanol or calcination up to 330° C.

The preceding Examples indicates that the apparatus, process and system of the present invention provides the following advantages:

Reaction time: Flow chemistry is able to produce MOFs at dramatically reduced reaction times, e.g. HKUST-1 in 1 min as opposed to 24 h using traditional methods, or NOTT-400 in 10 min rather than 72 h;

Space Time Yield: The Space Time Yield obtained by the process and apparatus of the present invention is 10 times larger than commercial employed methods; and Green chemistry principles: The present invention (reactor and megasonic separation) follow green chemistry principles leading to improved workplace safety and lower environmental impact.

Those skilled in the art will appreciate that the invention described herein is susceptible to variations and modifications other than those specifically described. It is understood that the invention includes all such variations and modifications which fall within the spirit and scope of the present invention.

Where the terms "comprise", "comprises", "comprised" or "comprising" are used in this specification (including the claims) they are to be interpreted as specifying the presence of the stated features, integers, steps or components, but not precluding the presence of one or more other feature, integer, step, component or group thereof.

The invention claimed is:

1. A process for producing metal organic frameworks, the process comprising:
    mixing at least two different precursor solutions for forming the metal organic framework (MOF) through inline mixing to form a solution mixture, the precursor solutions comprising a first precursor solution comprising at least one multidentate linking ligand in solvent; and a second precursor solution comprising a metal cluster or metallic salt thereof in solvent,
    introducing the solution mixture into an apparatus which comprises: a tubular flow reactor which comprises a tubular body having an inlet into which, in use, the solution mixture is fed and flows, said tubular body including at least one annular loop comprising a coil; and a flow restriction device comprising a back-pressure controller downstream of the tubular reactor for controlling the pressure within the tubular reactor, and promoting a reaction within the tubular flow reactor to form the metal organic framework,
    wherein the precursor solutions are mixed through inline mixing in a feed conduit fluidly connected to the inlet of the tubular body and the resulting solution mixture being fed into said inlet at room temperature, the two or more precursor solutions being mixed at or proximate said inlet,
    and wherein the solution mixture flows through said tubular body mixing the precursor compounds therein to produce the metal organic frameworks.

2. The process according to claim 1, wherein the apparatus further comprises an inline mixer located at or proximate the inlet to the tubular body, the inline mixer mixing the precursor solutions through inline mixing in said feed conduit fluidly connected to the inlet of the tubular body.

3. The process according to claim 1, further including the step of:
    applying a high frequency ultrasound of at least 20 kHz to a MOF containing solution sourced from the tubular flow reactor, thereby separating the MOF material from solution as an aggregated sediment which settles out of the MOF containing solution.

4. The process according to claim 3, wherein the yield of MOF from the apparatus is greater than 60%.

5. The process according to claim 1, wherein the tubular body comprises a heated tubular body in which the solution mixture is heated during flow through the said tubular body, said flow through said tubular body mixing the precursor compounds therein to produce the metal organic frameworks.

6. The process according to claim 5, wherein the tubular body is located inside a heated housing and the housing is heated via heating inlet and outlet port connections through which heated fluid is fed and extracted to heat the tubular body.

7. The process according to claim 5, wherein the tubular body heats the precursor compounds to a temperature of between 20 and 200° C.

8. The process according to claim 1, wherein the apparatus further includes a separator for separating a metal organic framework (MOF) from a solution, comprising:
    a housing having a reservoir capable of receiving a MOF containing solution; and
    a high frequency ultrasound transducer operatively connected to the reservoir and capable of applying megasonic frequencies of at least 400 kHz to the MOF containing solution.

9. The process according to claim 8, wherein the housing comprises a container including at least one wall position to contact the MOF containing, and the transducer is high frequency ultrasound transducer is position within the reservoir or in engagement with the at least one wall.

10. The process according to claim 8, wherein the housing includes at least one reflector surface designed to reflect the applied megasonic frequencies within the reservoir.

11. The process according to claim 8, wherein the applied high frequency ultrasound is at least one of:
    between 400 kHz to 4 MHz or
    greater than 1 MHz.

12. The process according to claim 8, wherein the applied high frequency ultrasound is at least one of:

between 600 kHz and 2 MHz; or
between 1 MHz and 4 MHz.

13. The process according to claim 8, wherein at least one contaminant includes occluded unreacted ligands within pores of the MOF.

14. The process according to claim 1, wherein the metal organic framework comprises a plurality of metal clusters, each metal cluster including one or more metal ions; and a plurality of charged multidentate linking ligands connecting adjacent metal clusters, and wherein the at least two different precursor solutions comprise a first precursor solution comprising at least one of the multidentate linking ligands; and a second precursor solution comprising a metal cluster or a metallic salt thereof.

15. The process according to claim 14, wherein each metal cluster comprises two or more metal ions and each ligand of the plurality of multidentate ligand includes two or more carboxylates.

16. The process according to claim 14, wherein at least one ligand of the plurality of multidentate ligand comprises an organic ligand which is at least bidentate and is selected from the group consisting of formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E,4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4-carboxylic acid, pyridine-3-carboxylic acid, imidazole, 1H-benzimidazole, 2-methyl-1H-imidazole, and mixtures thereof.

17. The process according to claim 14, wherein the metal ion is selected from the group consisting of Group 1 through 16 metals of the IUPAC Periodic Table of the Elements including actinides, and lanthanides, and combinations thereof.

18. The process according to claim 14, wherein the multidentate linking ligand has 6 or more atoms that are incorporated in aromatic rings or non-aromatic rings.

* * * * *